(12) United States Patent
Paulos

(10) Patent No.: US 9,364,333 B1
(45) Date of Patent: Jun. 14, 2016

(54) TRANSOSSEOUS METHODS AND SYSTEMS FOR JOINT REPAIR

(71) Applicant: THE LONNIE AND SHANNON PAULOS TRUST, Salt Lake City, UT (US)

(72) Inventor: Lonnie E. Paulos, Salt Lake City, UT (US)

(73) Assignee: The Lonnie and Shannon Paulos Trust, Salt Lake City, UT (US)

( * ) Notice: Subject to any disclaimer, the term of this patent is extended or adjusted under 35 U.S.C. 154(b) by 156 days.

(21) Appl. No.: 14/159,754

(22) Filed: Jan. 21, 2014

Related U.S. Application Data

(63) Continuation-in-part of application No. 13/436,968, filed on Apr. 1, 2012, now abandoned.

(60) Provisional application No. 61/756,099, filed on Jan. 24, 2013, provisional application No. 61/471,097, filed on Apr. 1, 2011.

(51) Int. Cl.
*A61F 2/40* (2006.01)

(52) U.S. Cl.
CPC .................................. *A61F 2/4014* (2013.01)

(58) Field of Classification Search
CPC ......................................................... A61F 2/40
USPC .................. 606/151; 623/18.11, 19.13, 19.14
See application file for complete search history.

(56) References Cited

U.S. PATENT DOCUMENTS

| 5,358,526 | A | 10/1994 | Tomeir |
| 6,514,274 | B1 | 2/2003 | Boucher et al. |
| 6,517,579 | B1 | 2/2003 | Paulos |
| 6,520,964 | B2 | 2/2003 | Tallarida et al. |
| 6,589,281 | B2 | 7/2003 | Hyde |
| 6,610,067 | B2 | 8/2003 | Tallarida et al. |
| 6,679,917 | B2 | 1/2004 | Ek |

(Continued)

FOREIGN PATENT DOCUMENTS

| WO | 2005016123 | 2/2005 |
| WO | 2006093763 | 9/2006 |

(Continued)

OTHER PUBLICATIONS

Araj, Michael J., Non-Final Office Action for co-pending parent U.S. Appl. No. 13/436,968, mailed Jul. 17, 2014, 10 pages, USPTO, Alexandria, VA.

(Continued)

*Primary Examiner* — Christopher Beccia
(74) *Attorney, Agent, or Firm* — John Brooks Law LLC; John J Brooks, III

(57) ABSTRACT

Methods and systems for transosseous access and repair of joint surface are disclosed wherein one embodiment of the method comprises inserting a reaming rod through a bone tunnel positioned perpendicular to a first joint surface, connecting a reaming blade to the reaming rod, reaming the first joint surface with the reaming blade and removing the reaming blade and the reaming rod. In some embodiments, the reaming blade is configured to be inserted into the joint through an arthroscopic access portal. In some embodiments, an implant system comprises an implant anchor and an implant surface cap and the implant anchor is adapted to couple with a fixation element to anchor the implant anchor in a bone.

20 Claims, 15 Drawing Sheets

(56) References Cited

U.S. PATENT DOCUMENTS

| | | | |
|---|---|---|---|
| 6,783,549 | B1 | 8/2004 | Stone et al. |
| 7,029,479 | B2 | 4/2006 | Tallarida et al. |
| 7,510,558 | B2 | 3/2009 | Tallarida et al. |
| 7,604,641 | B2 | 10/2009 | Tallarida et al. |
| 7,618,462 | B2 | 11/2009 | Ek |
| 7,713,305 | B2 | 5/2010 | Ek |
| 7,828,853 | B2 | 11/2010 | Ek et al. |
| 8,007,538 | B2 | 8/2011 | Gunther |
| 8,038,719 | B2 | 10/2011 | Gunther |
| 2002/0095214 | A1 | 7/2002 | Hyde, Jr. |
| 2005/0043805 | A1* | 2/2005 | Chudik .............. A61B 17/1684 623/19.14 |
| 2006/0195194 | A1 | 8/2006 | Gunther |
| 2007/0005074 | A1 | 1/2007 | Chudik |
| 2007/0016304 | A1 | 1/2007 | Chudik |
| 2007/0016305 | A1 | 1/2007 | Chudik |
| 2007/0027417 | A1 | 2/2007 | Chudik |
| 2007/0027477 | A1 | 2/2007 | Chudik |
| 2007/0037123 | A1 | 2/2007 | Mansueto et al. |
| 2007/0100353 | A1 | 5/2007 | Chudik |
| 2008/0021564 | A1 | 1/2008 | Gunther |
| 2008/0177334 | A1 | 7/2008 | Stinnette |
| 2008/0306601 | A1* | 12/2008 | Dreyfuss ............ A61B 17/1684 623/19.14 |
| 2009/0105838 | A1* | 4/2009 | Russo ................ A61F 2/30734 623/19.14 |
| 2009/0228049 | A1 | 9/2009 | Park |
| 2010/0023064 | A1 | 1/2010 | Brunger et al. |
| 2010/0087876 | A1 | 4/2010 | Gunther |
| 2010/0087877 | A1 | 4/2010 | Gunther |
| 2010/0249938 | A1 | 9/2010 | Gunther et al. |
| 2010/0268238 | A1 | 10/2010 | Sikora et al. |
| 2010/0268239 | A1 | 10/2010 | Sikora et al. |
| 2010/0274360 | A1 | 10/2010 | Gunther |
| 2011/0112648 | A1 | 5/2011 | Gunther |
| 2011/0166602 | A1 | 7/2011 | Malek |
| 2011/0166608 | A1 | 7/2011 | Duggal et al. |
| 2011/0282396 | A1 | 11/2011 | Shimko |
| 2011/0313533 | A1 | 12/2011 | Gunther |
| 2012/0109222 | A1 | 5/2012 | Goel et al. |
| 2012/0172996 | A1 | 7/2012 | Ries et al. |

FOREIGN PATENT DOCUMENTS

| | | |
|---|---|---|
| WO | 2008011078 | 1/2008 |
| WO | 2010121246 | 10/2010 |
| WO | 2010121250 | 10/2010 |
| WO | 2011112425 | 9/2011 |
| WO | 2012075183 | 6/2012 |

OTHER PUBLICATIONS

Depuy International Ltd, Marketing Brochure, Surgical Technique, Resurfacing Humeral Head Implant, Copyright 2004, pp. 3-22, DePuy International Ltd., Leeds England.

Depuy Orthopaedics, Inc, Marketing Brochure, Surgical Technique, Global FX, Shoulder Fracture System, Copyright 2009, pp. 4-41, DePuy Orthopaedics, Inc., Warsaw, IN, USA.

Synthes (USA), Marketing Brochure, Epoca Shoulder Prosthesis System. For hemi- and total-shoulder arthroplasty. Technique Guide, Copyright 2007, pp. 3-48, Synthes (USA), West Chester, PA, USA.

Arthrosurface, Inc., Marketing Brochure Page from Surgical Technique Guide, downloaded from www.arthrosurface.com about Mar. 2012, Arthrosurface Inc., Franklin, MA, USA.

Brian B. Johnson, Michael H. Santare, John E. Novotny and Suresh G. Advani, Wear Behaviour of Carbon Nanotueb/HighDensity Polyethylene Composites, NIH Public Access, Author Manuscript, Oct. 2009, 20 pgs., NIH Public Access, USA.

Prof. M. Randelli, "Mid-term results of a Metal Back glenoid in total shoulder arthroplasty", "Lima News" article, 2012, 4 pgs, Lima Corporate, Italy.

Shelain Patel, Fahad S. Hossain and Fares S. Haddad, "Bearing surfaces in lower limb total joint arthroplasty", The Journal of Bone and Joint Surgery, 2010, 4 pgs., British Editorial Society of Bone and Joint Surgery, UK.

Zimmer Inc., Collateral for Trabecular Metal Glenoid, downloaded from the World Wide Web Mar. 28, 2012 from URL http://www.zimmer.com/content/pdf/en-US/Trabecular_Metal_Glenoid_Surgical_Technique_97-4301-204-00_Rev_1_11_2009_US_ONLY.pdf. 20 pages.

\* cited by examiner

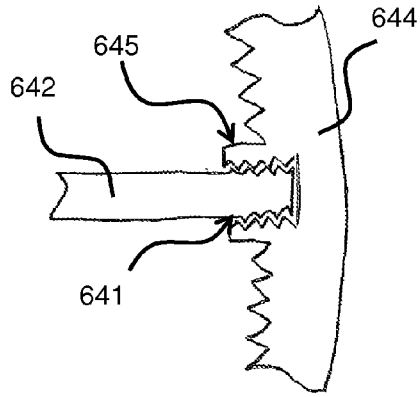
FIG. 6A
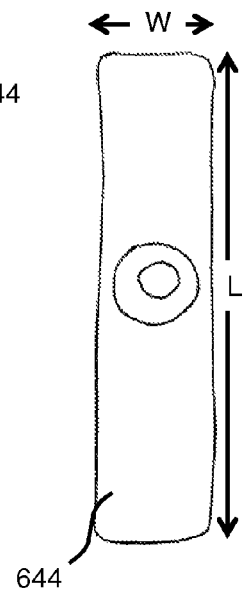
FIG. 6B
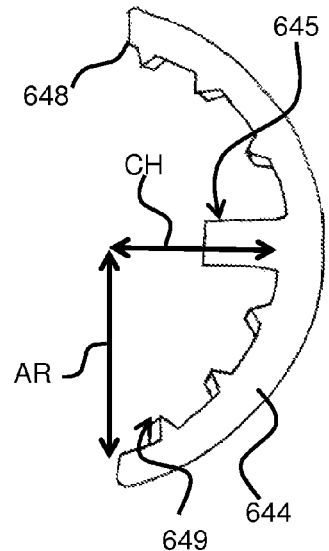
FIG. 6C
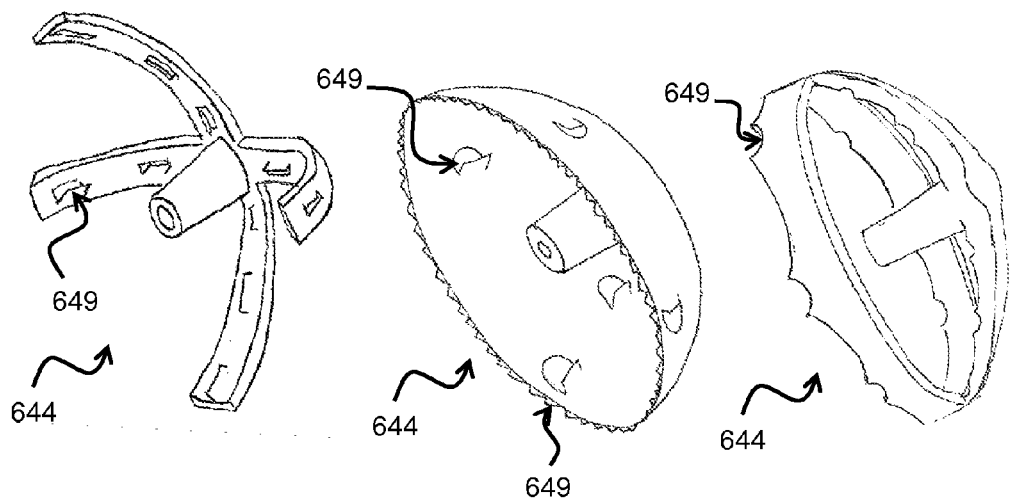
FIG. 6D  FIG. 6E  FIG. 6F

TRANSOSSEOUS METHODS AND SYSTEMS FOR JOINT REPAIR

CROSS-REFERENCE TO RELATED APPLICATIONS

This application claims benefit to U.S. Pat. App. No. 61/756,099 entitled TRANSOSSEOUS METHODS AND SYSTEMS FOR JOINT REPAIR filed Jan. 24, 2013 and this application is a Continuation-in-Part of co-pending U.S. patent application Ser. No. 13/436,968 entitled TRANSOSSEOUS METHODS AND SYSTEMS FOR JOINT REPAIR filed Apr. 1, 2012 which claims benefit of U.S. Pat. App. No. 61/471,097 entitled METHODS AND SYSTEMS FOR INTEROSSEOUS JOINT REPAIR", filed Apr. 1, 2011; all of the above applications are herein incorporated by reference in their entirety.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

1. Field of the Invention

This invention relates to methods and systems for performing joint repair. Particularly, these methods and systems are for performing joint repair using transosseous methods to access and repair the joint surfaces.

2. Description of the Prior Art

Methods for providing joint repair typically require radical access to the joint and the joint surfaces. These methods significantly increase the chance of damage to tissues around the joint and significantly increase the complications during and duration of recovery.

Common systems and methods currently in use today access the joint and joint surface from the surface side of the joint. One example of that is disclosed in U.S. Pat. No. 7,604,641 entitled "SYSTEM AND METHOD FOR JOINT RESURFACE REPAIR" to Tallarida et. al., filed Apr. 18, 2006 ("Tallarida"), which is herein incorporated by reference in its entirety. These procedures typically include both preparing the joint for the procedure and installing the implant.

The systems and methods of U.S. Pat. No. 6,589,281, issued Jul. 8, 2003 to Edward Hyde ("Hyde"), which is herein incorporated by reference in its entirety, attempt to address some of these issues by providing a transossesseous core approach to accessing a joint. Hyde discloses a system that preferably accesses the joint through a bone core that is later replaced after surgery. The methods include utilizing radical access through the bone, through a bone core, that is not consistent with a minimally invasive procedure.

The systems and methods of U.S. Patent Publication No. 2005/0043805, for U.S. patent application Ser. No. 10/917,266, filed Aug. 11, 2004 to Steven C. Chudik ("Chudik"), which is herein incorporated by reference in its entirety, attempt to address shoulder replacement surgery while sparing the rotator cuff. However, the surgical methods disclosed address total replacement or hemiarthroplasty which are also radical procedures that are not necessarily needed in all instances. Additionally, the disclosed systems and methods utilize anchoring systems that are installed from the joint side of the transhumeral bone tunnel.

What is not disclosed are a minimally invasive procedures and tools that allow focused joint repair utilizing a transosseous approach.

What is also not disclosed are implant systems that utilize the anchoring features provided in a transosseous approach to joint repair.

BRIEF SUMMARY OF THE INVENTION

Example embodiments of transosseous systems and methods for joint repair provide a way to provide joint repair in a minimally invasive manner.

In some embodiments, a method of performing a joint repair is provided comprising the steps of reaming a transosseous bone tunnel extending through to a first joint surface, inserting a stem of a first implant in the bone tunnel and anchoring the stem from a proximal end of the bone tunnel. In some embodiments, the methods further comprises the steps of positioning a reaming rod through the bone tunnel after reaming the bone tunnel, connecting a first reaming blade to the reaming rod and reaming the first joint surface with the first reaming blade before inserting the stem of the first implant in the bone tunnel. In some embodiments, the step of anchoring the implant from a proximal end of the bone tunnel further comprises inserting a fixation element into the bone tunnel, ensuring the stem is secured to the first implant and engaging the stem with the fixation element whereby the fixation element anchors the first implant on the first joint surface. In some embodiments, the method further comprises, after reaming the first joint surface and before inserting the stem of the first implant in the bone tunnel, the steps of removing the first reaming blade from the reaming rod, ensuring the bone tunnel is perpendicular to a second joint surface, connecting the second reaming blade to the reaming rod, reaming the second joint surface, removing the second reaming blade from the reaming rod, removing the reaming rod from the bone tunnel, placing a second implant on the second joint surface and securing the second implant on the joint surface.

In some example embodiments, an implant system is provided comprising a fixation element having a fixation element stem end and a fixation element head end, a stem having an stem implant end and a stem fixation element end, the stem fixation element end configured to engage the fixation element stem end and the fixation element is configured to anchor the stem in a bone when the fixation element stem end engages the stem fixation element end. In some embodiments, the fixation element is configured to anchor the stem in a bone tunnel, the bone tunnel has an implant end and an opposite end and the fixation element is configured to engage the stem from the opposite end of the bone tunnel. In some embodiments, the fixation element stem end has a tapered outer periphery, the stem fixation element end comprises an outer surface and an internal bore configured to receive a portion of the fixation element stem end and the stem fixation element end is configured to expand when the portion of the fixation element stem end is received in the internal bore of the stem whereby the outer surface of the stem fixation element end engages the bone and anchors the stem in the bone. In some embodiments, the tapered outer periphery further comprises an external threaded portion. In some embodiments, the fixation element end of the stem comprises an outer surface and a tapered internal bore configured to receive a portion of the fixation element stem end and the stem fixation element end is configured to expand when a portion of the fixation element stem end is received in the internal bore of the stem whereby the outer surface of the stem fixation element end engages the bone and anchors the stem in the bone. In some embodiments, the fixation element stem end further comprises an externally threaded portion and the internal bore of the stem comprises a internally threaded portion configured to receive the external threaded portion of the fixation element stem end. Some embodiments further comprise an implant having a coronal surface and a stem connecting portion configured to connect to the stem implant end of the stem. In some embodiments, the fixation element is configured to anchor the stem in a bone tunnel, the bone tunnel having an implant end, an opposite end and a tunnel diameter and the fixation element head end having an outer diameter or outer peripheral edge greater than the tunnel diameter whereby when the fixation element engages the stem and the fixation element head end anchors the stem in the bone.

In some example embodiments, a transosseous system is provided to ream a joint surface, the system comprising a reaming blade having a blade edge defining and axial radius and a reaming surface having a center and a central height from the blade edge, a reaming rod having a proximal end and a joint end, the reaming rod configured to access a first bone surface of a joint through a bone tunnel having a proximal end and a joint end and a blade connecting portion on the reaming blade capable of removeably connecting to a rod connecting portion on the joint end of the reaming rod whereby rotation of the reaming rod at the proximal end of the bone tunnel rotates the reaming blade to ream the first bone surface. In some embodiments, the reaming surface of the reaming blade comprises a plurality of protrusions extending from the reaming surface. In some embodiments, the reaming blade further comprises a reaming limit marker. In some embodiments, the reaming surface has a concave shape, the reaming surface having a central height of about 10 to 60 mm and an axial radius of about 5 to 30 mm and the reaming blade is configured to fit through an access portal and within a joint. In some embodiments, the reaming surface has a concave elongated shape, the reaming surface having a central height of about 10 to 60 mm and an axial radius of about 5 to 30 mm, the reaming blade has a width of about 10 to 20 mm and a length of about 10 to 60 mm and the reaming blade is configured to fit through an access portal and within the joint. In some embodiments, the reaming surface has a convex shape with a central nipple, the reaming surface having a central height of about 10 to 60 mm and an axial radius about 5 to 30 mm and the reaming blade is configured to fit through an access portal and within the joint. In some embodiments, the transosseous system further comprises a sleeve having a longitudinal bore sized to receive the reaming rod and an external diameter sized to secure the sleeve in the bone tunnel.

In some example embodiments, an implant system is provided wherein the implant comprises an implant anchor and an implant surface cap. In some embodiments, the implant system comprises an implant anchor having an anchor retaining element, an implant surface cap with a cap retaining element and the cap retaining element is configured to couple with the anchor retaining element whereby the implant surface cap can be secured to the implant anchor. In some embodiments, the implant system further comprises a stem, a fixation element, the stem having a fixation element end and an anchor end, the anchor end of the stem configured to couple with the implant anchor and the fixation element having a stem end configured to couple with the fixation element end of the stem whereby when the fixation element is secured to a bone, the fixation element secures the stem and the implant anchor to the bone. In some embodiments, the implant system is configured to be used as a humeral head implant.

In some example embodiments, an implant system is provided comprising an implant anchor having a anchor retaining element, an implant surface cap with a cap retaining element, the cap retaining element is configured to couple with the anchor retaining element whereby the implant surface cap is coupled to the implant anchor and the implant system is configured to be used as a glenoid implant.

In some example embodiments, a method of performing a joint repair is provided comprising the steps of reaming a transosseous bone tunnel extending through to a first joint surface, inserting a stem of a first implant anchor in the bone tunnel, positioning an implant anchor on the first joint surface, securing the stem to the implant anchor, securing an implant surface cap to the implant anchor and anchoring the stem and the implant anchor from a proximal end of the bone tunnel.

Additional embodiments and features of the invention will become apparent to persons skilled in the art to which the invention pertains from the following detailed description and claims.

This summary is not comprehensive and is not intended to delineate the scope of protectable subject matter, which is set forth by the detailed description and the claims presented at the end.

BRIEF DESCRIPTION OF THE SEVERAL VIEWS OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 6A illustrates a cut away side view of one example embodiment of the reaming rod and reaming blade showing details of their connecting means;

FIGS. 6B and 6C are top and side views respectively detailing the reaming blade of FIG. 6A;

FIGS. 6D-6F illustrate bottom perspective views of example embodiments of a reaming blade for convex joint surfaces;

DETAILED DESCRIPTION OF THE INVENTION

Figure 1A:
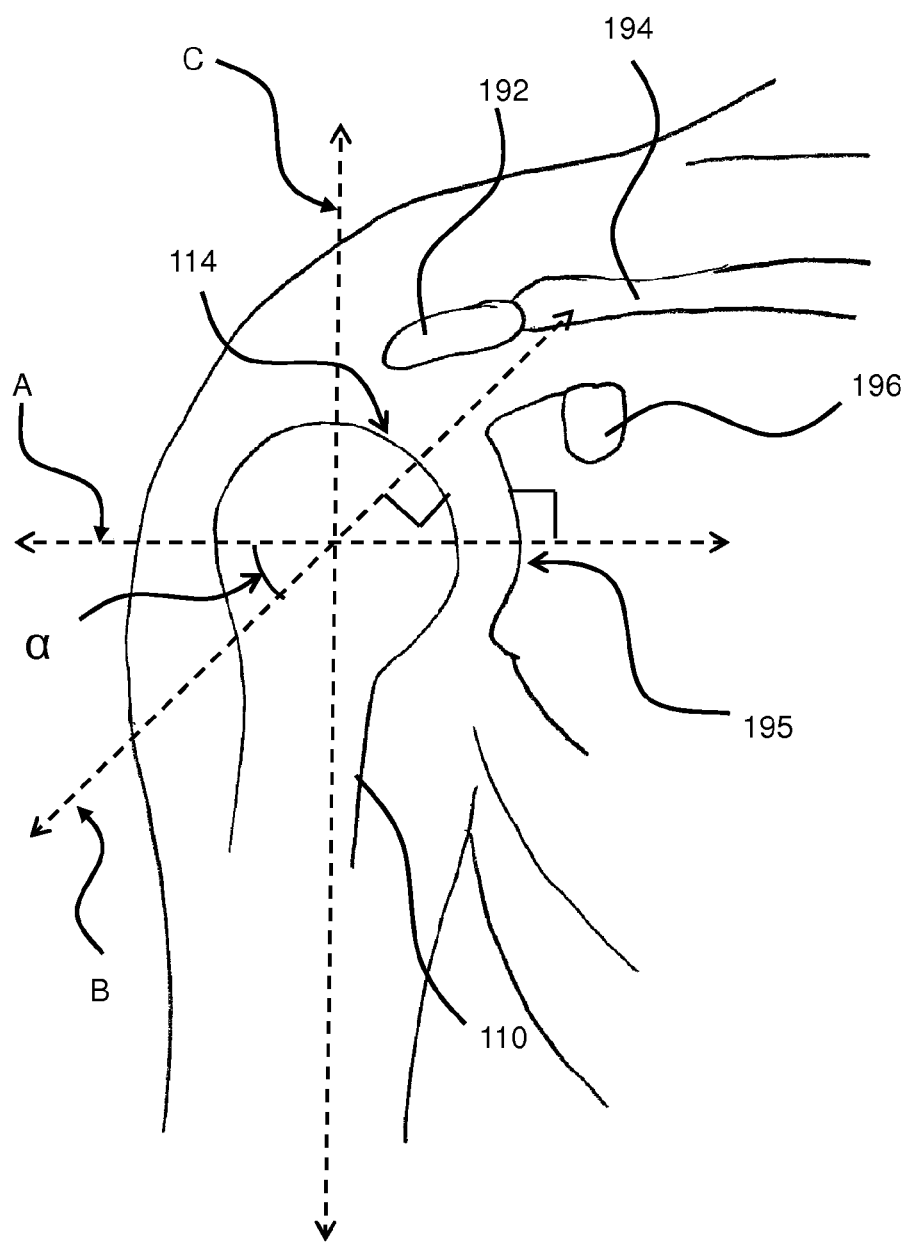
FIG. 1A is a front illustration of the bone anatomy around a shoulder joint and showing axes utilized in the systems and methods disclosed.

Systems and methods to provide transosseous access and repair of mammalian joints will now be described in detail with reference to the accompanying drawings Utilizing the methods and systems of the present invention, minimally invasive access can be provided to one or more joint surfaces so that a focused repair of the joint surface can be performed. Preferably, the methods utilize arthroscopic methods and novel tools to help provide access to the joint. Optionally the systems and methods described may also be used in open surgical procedures.

Generally, one embodiment of the methods of the invention utilize among other things: arthroscopic access to the joint; limited incisions; conventional or novel transosseous repair tools with modular working elements; and conventional or novel implant systems and elements for joint repair. The methods generally follow the steps of accessing the joint, identifying a first joint reference point, reaming a transosseous bone tunnel through the bone to the first surface reference point, configuring a reaming blade on the joint surface that cooperates with a transosseous reaming rod, reaming the joint surface, removing the reaming tools, installing the implant on the joint surface and closing the surgical site. In some embodiments, multiple joint surfaces are repaired. In these embodiments, the joints are aligned, and typically put into traction, such that the repair areas are aligned. Once aligned, the methods can be applied to both surfaces through a single transosseous bone tunnel through one of the bones of the joint. Reaming can be done through the single tunnel which can be used to provide access to position and anchor implants on both joint surfaces.

Preoperative procedures can be performed utilizing radiographic images or CT scans to provide the surgeon with information that can be used to size the tools, size the implants, position reference points and position the tunnels that may be used.

According to the methods of one embodiment of the present invention, either before or after the joints are positioned and put into traction, arthroscopic access to the joint is provided utilizing common arthroscopic portals. In this arthroscopic embodiment, a reference point is then defined on one of the joint surfaces that will define an access point on the first joint surface. This reference point will preferably be positioned to allow generally perpendicular access through a transosseous bone tunnel to the first joint surface. The reference point may also be positioned such that it allows generally perpendicular access to a joint surface on a second joint surface to be repaired. The positioning of the reference point should generally be at the center of the area to be repaired however, the reference point need not be at the center of the entire joint surface.

A drill guide is then used to position insertion of a guide pin through the first bone such that it is aligned with the reference point and is generally perpendicular to the first joint surface, at the reference point, to be repaired. Positioning of the drill guide element is done carefully to avoid nerves around the joint. For embodiments that will repair portions of the first and second joint surface, the alignment of the tunnel on the first joint surface is aligned so that a bone tunnel can be created that generally provides perpendicular access to both joint surfaces to be repaired. This alignment can be provided by putting bones in the joint through some degree of rotation or abduction during the repair. Traction may also be applied to the joint to provide more access to the space between the joint surfaces.

Using the positioned guide pin and standard arthroscopic procedures, a bone tunnel is then created to the reference point on the first joint surface. This is typically done by placing a reamer over the guide pin and reaming a tunnel over it. After removing the reamers and the guide pins, a cannulated sleeve is secured proximal to the bone tunnel on the side opposite of the joint surface. Typically this sleeve is secured partially through the bone and extends out of the bone and through a stab or portal in the skin. The sleeve is typically sized with a longitudinal bore sufficient to receive the reaming rod and an external diameter sized to secure the sleeve within the walls of the bone tunnel. In some embodiments the sleeve is positioned prior to the creation of the bone tunnel. In these embodiments, the sleeve extends through the portal in the skin and be secured to the bone with external securing means. Once the sleeve is secured, the bone tunnel is reamed aligned with installed guide pin.

The result of these steps is a sleeve providing access from the outside of the skin to a proximal end of the bone tunnel and through the bone tunnel extending to the joint surface. The sleeve may extend through the skin and partially or totally extend through the bone tunnel providing transosseous access to the joint surface to be repaired. In this example, the first joint surface is being repaired and a reaming system is used to ream the surface.

The reaming system comprises a reaming blade configured to fit between the joint surface, a removable reaming rod configured to access a joint through the tunnel and sleeve and a means to connect the reaming blade to the reaming rod whereby a rotation of the reaming rod rotates the reaming blade.

Through the tunnel and sleeve, the reaming rod is inserted. The reaming rod has a reamer end to removably connect the rod to a reamer and a blade end having means for removably connecting the rod to the reaming blade. The means of connecting can be any means to removably connect or couple the reaming rod end to the reaming blade while also allowing for later separation of the elements. Any removable connection means is suitable that removably connects the reaming blade and the reaming rod and allows the reaming rod to rotate the reaming blade. Suitable connecting means include, but is not limited to, mating connections such as threaded, friction, push pin, clipped or pinned connections that can be connected and disconnected in a confined space. In a preferred embodiment, the means of connecting is a threaded connection that cooperates with the rotation of a reamer so that the connection is not urged to release while reaming is being performed but can be easily unthreaded when needed.

At some point of the methods prior to insertion of the reaming blade, an access portal is created though the skin to provide access to the joint. Through this access portal, the selected reaming blade can be inserted and connected with the reaming rod so that the rod can be used to move the blade. The reaming blade has a mating connection portion that mates with a mating connection portion of the reaming rod as described above. The reaming blade is shaped and has a reaming surface such that through movement of the blade, such as a circular motion about the rod, the reaming surface will engage with the joint surface and remove portions of the joint surface to be repaired.

It is possible to have many reaming blade shapes and types of reaming surfaces. In one embodiment, the reaming blade shape is generally convex shaped to ream concave joint surfaces with a central bore. In another embodiment, the reaming blade surface is generally concave to ream convex joint surfaces. Embodiments of reaming blades may be elongated, but could be any shape that provides for reaming of a joint surface with a motion such as a rotary motion of the blade about the end of the rod.

In one embodiment, the end of the reaming rod exposed to the joint is a mating connecting portion that mates with the mating connecting portion of the reaming blade allowing the two elements to be connected and be used to ream the joint surface. In this embodiment, the connecting portions are threaded portions that connect the reaming rod with the reaming blade.

Once connected, the reaming rod and reaming blade are used to ream the joint surface to a predetermined depth limit. This is done by attaching the end of the reaming rod to a reamer so that the reamer will rotate the reaming blade. By rotating the reaming rod and reaming blade and putting a properly directioned force on the reamer, the reaming blade engages the joint surface being repaired. The depth limit for reaming can be made visually, with or without the assistance of reaming markers, can be restricted by cooperation of the sleeve in the tunnel or it can be restricted by the design of elements such as the reamer surface. Either joint surface may be reamed.

The result of this reaming is typically a joint surface that has had the articular cartilage of the joint surface removed down to bleeding subchondral bone.

During these steps of the methods, bone debris from the bone and joint surface reaming may be removed by common arthroscopic procedures such as with irrigation and suction.

With the joint surface reamed, the reaming blade may be removed from the reaming rod by undoing the connection between the two elements. These elements are typically removed by reversing the method of connecting the elements, such as reversing the direction of rotation for a treaded connection. Some embodiments may be directed to repair a single joint surface. With the joint surface reamed, an implant can be applied to the joint surface. The implant can be inserted through the access portal and may be secured to the surface using common implant securing means such as adhesives such as Poly(methyl methacrylate) (PMMA) cement or mechanical means. One embodiment of a securing means is to utilize the tunnel and a fixation element to anchor elements of the implant. For example, an implant with a threaded collar, or stem, can be secured to the bone by a mating threaded fixation element that anchors the stem and implant in the bone. Some implants may also be secured through other orthopedic securing means. For example, the implant can be secured to the joint surface utilizing pegs and cement, or a keel and cement or anchors with locking screws.

For cemented connections, the irrigation may be stopped and the joint may be given an opportunity to dry.

For embodiments that require multiple surfaces to be repaired, a second joint surface can be prepared during the above steps at some point prior to securing the implant that obstructs the bone tunnel. For these embodiments, the tunnel in the first joint bone is maintained in alignment with the second joint bone and surface such that the axis of the first tunnel is also generally perpendicular to the second joint surface. Through this alignment, a reaming rod is also positioned in the first tunnel and a reaming blade is connected to ream the second joint surface. For multiple joint surface applications, one of the joint surfaces will likely be convex while the other will likely be concave. A convex surface will generally require a concave reaming surface and a concave surface will generally require a concave reaming surface. A reaming blade with the appropriate reaming surface shape is selected and used to ream the second joint surface down to subchondral bleeding bone. The reaming blade and rod are then removed and an implant is applied to both the first and second joint surface. For the second joint surface, because it is typically does not have a through tunnel, the implant may also be secured through the normal means to secure joint implants. In addition to those means, the joint may be prepared, and the implant may be secured with anchor means that are passed through, or secured using tools that pass through the first bone tunnel. For example, and not for limitation, the joint can have anchor holes drilled with drill elements passing through the bone tunnel. Similarly, the implant can be secured with anchor screws tightened with tools passing through the bone tunnel, with keels impacted with tools through the bone tunnel or with adhesives securing the implant into recesses created by tools passing through the bone tunnel.

One example embodiment of transosseous implant systems utilized in these methods generally includes an implant, an implant stem and a fixation element. These transosseous implant systems are secured using access to implant elements through the bone tunnel from the side opposite the joint surface.

One example embodiment of transosseous implant systems utilized in these methods generally includes an implant anchor, a surface cap, an implant stem and a fixation element.

One example embodiment of the transosseous implant systems has the implant configured to rest on the repaired surface. The implant may be integral with, or may be connected to the stem that extends from a bottom surface of the implant and extends into a portion of the bone tunnel when implanted. The stem is configured to connect to the fixation element such that when the fixation element is connected, the implant stem and the implant are anchored in the bone tunnel.

Implants for use with these methods may be sized during the surgery or they may be determined during the preoperative procedures described. Implants elements may be coated with an ingrowth surface or ingrowth material to promote bone growth and adhesion of the implant elements to the bone surfaces after surgery.

The result of the above methods is a joint having one or more joint surfaces prepared using minimally invasive means and implants secured to the joint surfaces in a minimally invasive manner.

Although the above procedures are described in an arthroscopic embodiment, it is understood that the methods and systems described can be used with open surgical techniques as well.

One Embodiment of Transosseous Methods and Systems for Joint Repair:

In order to further illustrate the present invention, one embodiment is described using an example embodiment of applying the methods disclosed on a large joint, in particular, the shoulder joint. It will be appreciated that, while the following description focuses on an assembly for use with a shoulder joint, the systems and methods disclosed herein have wide applicability. For example, the methods and apparatus described herein may be readily employed with other joints such as a knee, an elbow, a hip or an ankle. Notwithstanding the specific example embodiments set forth below, all such variations and modifications that would be envisioned by one of ordinary skill in the art are intended to fall within the scope of this disclosure.

In this example embodiment, the process of transosseous joint repair involves steps similar to those described above. These steps include gaining access to a joint through minimally invasive means, creating a bone tunnel, inserting a reaming rod through the bone tunnel positioned perpendicular to a first joint surface, connecting a reaming blade to the reaming rod, reaming the first joint surface with the reaming blade, removing the reaming blade and the reaming rod and securing an implant to the joint surface. These methods may be used to repair a single joint surface or they may also be used for, as will be illustrated, a process of repair for two joint surfaces such as surfaces of a human shoulder.

Figure 1B:
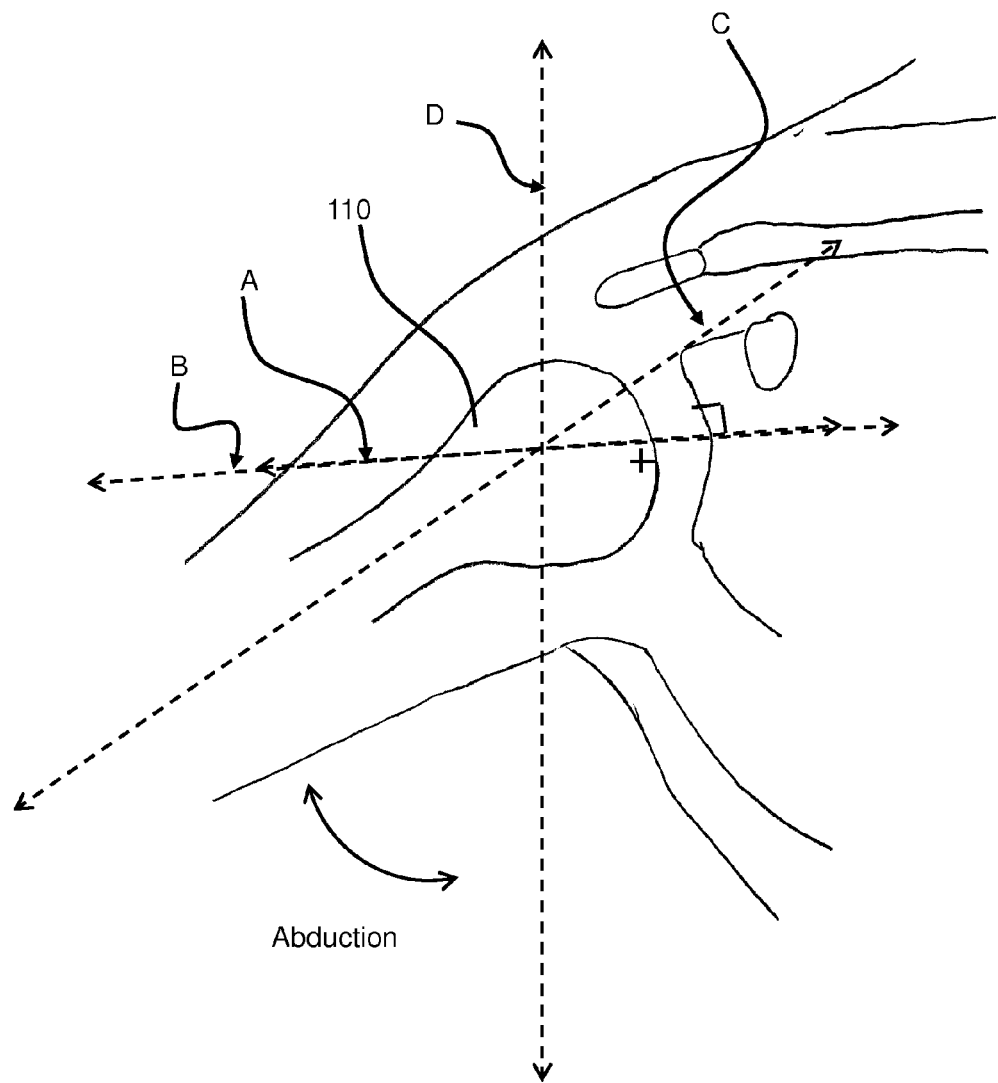
FIG. 1B is a front illustration of the bone anatomy of a should joint with an abducted humerus showing axes utilized in the systems and methods disclosed.

Illustrated in FIGS. 1A through 13 are embodiments of transosseous systems and methods of performing joint repair on a shoulder joint according to one embodiment of systems and methods of the present invention. As shown in FIGS. 1A and 1B, the shoulder joint anatomy involved in a shoulder joint repair includes the humerus 110, glenoid 195, scapula, acromion 192, clavicle 194 and the coracoid 196. In this illustration, the humerus is positioned alongside the patient's body and the methods described for the shoulder take advantage the natural relationship between the orientation of the humeral and glenoid surface of this joint. Referring to FIG. 1A, Axis A is defined as being perpendicular to a surface point of the glenoid face generally at the glenoid face center. Axis B is defined as an axis perpendicular to the reference point on the humerus head surface 114. The two axes generally cross in the rotational center of the humerus head. The angles related to the joint anatomy will be specific to each patient, but in this illustrative embodiment, when each of the reference points are positioned at the center of their respective joint surfaces and the humerus in not abducted, the angular difference a between axes A and B is generally 30 to 70 degrees or about 45 to 60 degrees. These two axes are generally in a position such that when the centerline of the humerus (C in FIG. 1B) is put in a similar angle of abduction, as shown in FIG. 1B, the two axes are brought into alignment and line up the centers of the opposing articular surfaces.

Prior to performing the methods of the joint repair, consistent with the earlier description, preoperative procedures can be performed such as taking and reviewing X-rays, CT scans or MRIs of the joint to help determine the size of tools needed, positioning of bone surfaces, size of implants or provide other diagnostic information. The surgeon's selection of equipment to include the sizing of tools and implants will be based on the surgeon's experience.

At the start of the procedures, the patient is positioned using a holding means that allows the bones of the joint to be moved and positioned without excessive restriction. The patient is placed in the lateral decubitus position and the arm of the shoulder being repaired is facing upward. The arm is available for being suspended in traction towards the ceiling. The traction system is adjustable and allows the surgeon to position the humerus relative to the glenoid.

Arthroscopic portals are established when and where deemed necessary by the surgeon. In a preferred embodiment, portals will be created in the following types of positions: posterior portal, anterior-superior portal and anterior interval portal. The arthroscope can be placed in the posterior portal so that an arthroscopic determination can be made that a repair of a joint is necessary using conventional arthroscopic procedures. The anterior interval portal can be used to debride soft tissue, remove loose bodies, remove inferior humerus head spurs and peri-glenoid osteophytes if desired.

Before or after creation of the portals, the surgeon will position the arm. Referring to FIG. 1B, the humerus 110 is abducted and put in traction such that the pin (line A) is then perpendicular to the articular surface of the glenoid, (line B). To properly position the first and second joint surfaces for these procedures, the humerus 110 is placed in abduction from axis D with care not to rotate, flex or extend it. The abducted position can be estimated visually or an x-ray machine can be used to confirm the position of the pin to the glenoid. There is usually enough motion in the shoulder to allow fine adjustments. The abduction angle is dependent on the position of the arm and its relationship to the scapula. To position the humerus such that the path of the transhumeral portal is perpendicular and centered on the glenoid surface to be repaired, the humerus may also need to be rotated and/or laterally distracted. Traction may also be applied to the arm as determined by the surgeon to provide additional space between the joint surfaces. Traction such as about 10-20 lbs or 15-20 lbs is usually sufficient. The arm has to be consistently positioned and adjusted at each surgery.

The angle of abduction will be specific to each situation, but in one embodiment, the angle may be between about 30 and 60 degrees or about 40 to 50 degrees or about 45 degrees.

Using a drill guide with a guide tip end and a cannulated end, the guide tip is placed in the center of the portion of the humeral head to be repaired using the anterior-superior portal. The guide arm point is positioned in the center of the repair location, for this illustration the center of the humerus articular surface, and the guide pin is then drilled from lateral to medial, starting at the mid-deltoid location. This is preferred because if the guide pin is drilled too low, the axillary nerve may be damaged. The positioning of the bone tunnel should reflect an angle that is perpendicular to the humeral head surface at the point the tunnel exits the humeral head surface. Then, the cannulated end of the drill guide brought to the lateral deltoid and a stab wound is made with care to avoid the axillary nerve. The cannulated end of drill guide is pushed through the wound to the lateral humerus cortex. If necessary, the deltoid can be carefully and bluntly split along the muscle fibers to allow the drill guide to securely seat on the humerus cortex with minimal damage to the deltoid muscle.

Figure 2A:
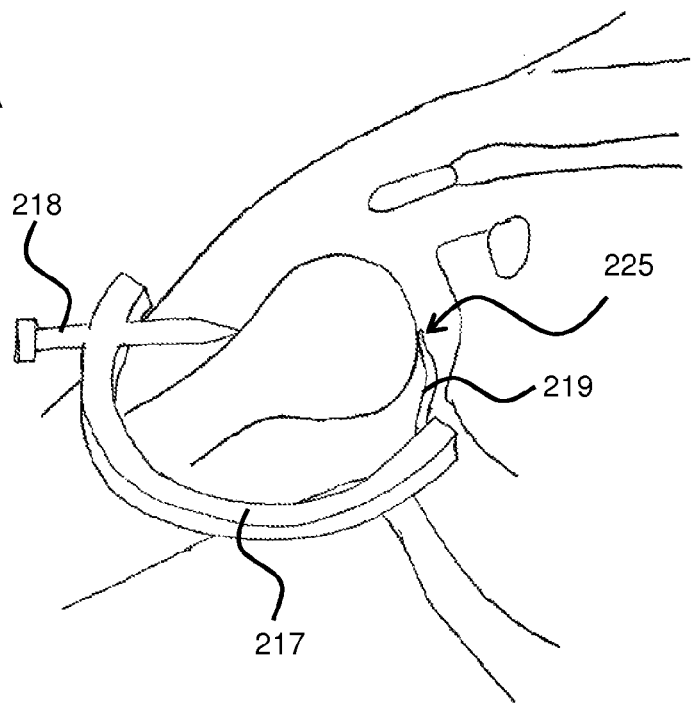
FIG. 2A illustrates one embodiment of a drill-guide and its alignment in positioning a transosseous bone tunnel.

As illustrated in FIG. 2A, a transhumeral drill guide 217 may be used. The drill guide shown is a U or C-shaped guide that allows a guide tip 219 to be positioned on the humeral head while a cannulated end 218 can be positioned on the lateral humerus cortex. The guide tip end is sufficiently rigid and narrow with a tip that can frictionally engage the joint surface and serve as a reference point for positioning a guide pin aligned with the center of the repair surface as 225. The cannulated end 218 is a generally bullet shaped end having a longitudinal bore aligned with the guide tip. The bore of the cannulated end can guide a guide pin to generally intersect with the tip of the guide tip 219.

Another embodiment of a suitable drill guide that can be modified to serve as a drill guide is described in co-pending U.S. application Ser. No. 12/937,402 entitled "LIGAMENT RECONSTRUCTION GUIDE ASSEMBLY AND METHODS OF USE" with a filing date of Oct. 20, 2010 and a 371 Entry Date of Oct. 12, 2010, which is herein incorporated by reference in its entirety. This embodiment of the drill guide can be configured to have the guide tip end of the guide access the humeral head with minimal tissue disruption. As discussed above, the placement of guide pins, reference points, or center of the humeral head if necessary, may be determined using the dimensions from diagnostic scans, such as CT scans or X-Rays, prior to or during surgery.

With the drill guide tip positioned on the humeral head surface as described above and the cannulated end of the drill guide positioned on the lateral humerus cortex, a guide pin is drilled. In one embodiment, a 2.8 mm guide pin is drilled to the tip of the U-shaped drill guide of FIG. 2A at the center of the humerus head. The guide pin may have any dimension as determined by the surgeon. In some embodiments, guide pin's sized with diameters between 2 mm and 3 mm and lengths of about 13 cm to 30 cm are suitable. In one embodiment, the guide pin is sized at 2.3 mm and is 20 cm long. The arthroscope can also be used to assure proper guide pin angle to the glenoid if a portion of the guide pin extends through the articular surface of the humeral head.

Referring back to FIG. 1B, the surgeon may further adjust the humerus 110 after a guide pin is placed along line A such that the guide pin aligned with axis A is then perpendicular to the articular surface of the glenoid, axis B. This position can be estimated visually or an x-ray machine can be used to confirm the position of the guide pin to the glenoid. There is enough motion in the shoulder to allow fine adjustments and the arthroscope can be used to assure proper pin angle to the glenoid.

Figure 2B:
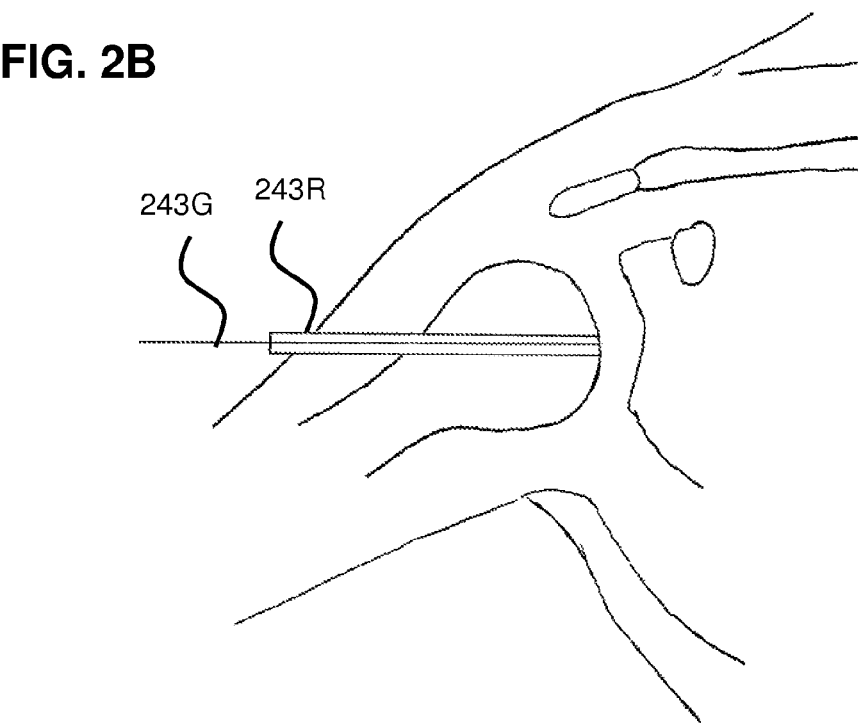
FIG. 2B illustrates the general positioning of an example embodiment of a reamer and portal guide pin as utilized in the disclosed systems and methods.

As illustrated in the embodiment of FIG. 2B, the guide pin 243G is then reamed over with a cannulated reamer 243R to create a through tunnel from the lateral humerus cortex to the humeral head surface. The size of the reamer 243R can generally be any size that will ream over the positioned guide pin 243G. Examples of suitably sized reamers in some embodiments include those sized between about 4 and 8 mm in diameter and about 12 to 25 cm long. In one embodiment, the reamer is about a 5.5 mm cannulated reamer about 18 cm in length.

In one embodiment, the guide pin is reamed over with additional reamers to create a sleeve tunnel in addition to the through tunnel. The sleeve tunnel does not have to extend to the head surface and preferably only extends into the humerus head to a dimension of about 2 to 3 cm or more preferably about 2.5 cm. The through tunnel is reamed as described above and the sleeve tunnel can be created before or after the through tunnel is reamed.

If the sleeve tunnel is created before the through tunnel, this is created by a cannulated sleeve reamer that goes over the guide pin and creates a tunnel into the humerus head. After this sleeve tunnel is created, the through tunnel reamer is positioned within the sleeve reamer and reams the through tunnel to the joint surface. The sleeve reamer can be sized sufficiently to go over the guide wire and be large enough to have the through tunnel reamer fit within. In some embodiments, the sleeve reamer can be about 6 to 8 mm in outside diameter and about 12 to 25 cm long. In one embodiment, the sleeve reamer is about a 7 mm diameter reamer with a length of about 18 cm.

Figure 4:
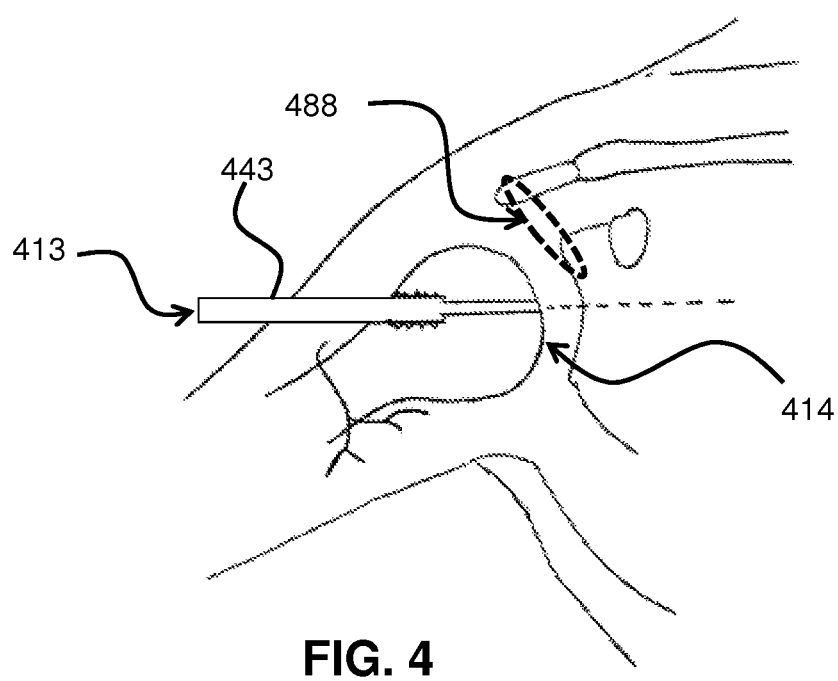
FIG. 4 illustrates the general position of an example embodiment of an access portal and another embodiment of a transosseous bone tunnel with a threaded sleeve positioned in the proximal end of the bone tunnel.

With the sleeve tunnel reamed and the bone tunnel reamed, the guide wire is then removed and a threaded sleeve may be passed over the sleeve reamer and secured to the bone tunnel. As shown in FIG. 4, the threaded sleeve 443 is passed over the reamer and screwed into the humeral head until secure. The sleeve has a larger inside diameter than the outside diameter of the sleeve reamer. Dimensions of example sleeves are about 6 to 8 mm insider diameter and about 6 to 10 cm long. In one embodiment, the sleeve has an inside diameter of 7 mm, is 8 cm long and is secured 2.5 cm into the humerus. As shown, the other end of the sleeve 443 is dimensioned to extend through the tissues of the arm and out of the skin through a portal. In some embodiments, the sleeve 443 will actively be used to help guide the depth of reaming done with these methods. In some embodiments, the sleeve 443 is marked with reference lines that can be aligned with reference points or lines on other tools, such as the reaming rod, so that the position of the reaming rod relative to the anchored sleeve can be determined. In some embodiments, the sleeve contains physical barriers that cooperate with physical features of other tools so that together they function to control and limit the movement of tools such as the reaming rod relative to the sleeve.

Figure 3:
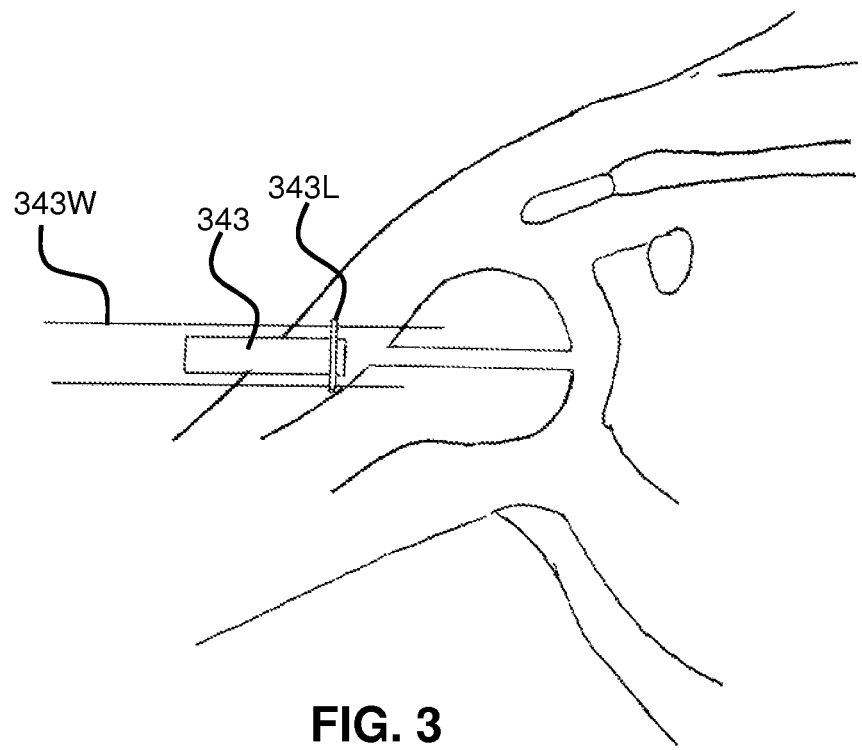
FIG. 3 illustrates one example embodiment of a transosseous bone tunnel and a sleeve secured to the later humerus cortex.

In some embodiments, the sleeve is not secured in the bone or sleeve tunnel, but is secured to the lateral humerus cortex with a lip around one end of the sleeve and threaded wires. One example of this is shown in FIG. 3 which illustrates an embodiment of the sleeve 343 with threaded wires 343W that may be secured to the humerus and they can also be secured to threaded holes in the lip 343L such that the sleeve lip 343L is secured to the bone. This type of sleeve embodiment may be installed before or after the bone tunnel is reamed.

Once the sleeve is secured, the reamers are removed. As shown in FIG. 3, the sleeve 343 may be secured to the lateral cortex with threaded guide wires 343W. As shown in FIG. 4, the threaded sleeve 443 may partially extend into the bone tunnel 413.

At this point, using the example shown in FIG. 4, a tunnel 413 has been created through the humerus providing access through a portal in the arm skin, through the humerus lateral cortex to the humeral head articular surface 414. A portion of the tunnel 413 may be lined with the sleeve 443 extending out of the skin of the patient to minimize damage to the bone and surrounding tissues during the repair. This tunnel 413 can be used to repair a single joint surface and the tunnel may also be used to access and repair a second joint surface as described below.

Once the humerus is positioned and secured with the bone tunnel created and the sleeve secured, the reaming rod is passed through the tunnel while viewing with arthroscope posterior so that the securing end of the reaming rod is positioned towards the surface of the joint. The reaming rod can be any size that will fit within and extend out of the sleeve and fit within the through tunnel. In one embodiment, the reaming rod is a 4.5 mm threaded rod which may or may not be cannulated. In some embodiments, the reaming rod is calibrated and marked such that its position related to landmarks, such as the end of the tunnel sleeve, can be determined.

At some point in the procedure, the anterior-superior portal 488 is sized to ensure it can pass a reaming blade, as shown in FIG. 4. If this portal needs to be enlarged as the access portal, it is done with care not to damage the rotator cuff or biceps tendon. In one embodiment, the anterior-superior portal 488 is enlarged to create an anterior rotator cuff interval. In embodiments, the portal may need to be enlarged to accommodate the reaming blade and the surface implants. For some embodiments, the portal is enlarged by an incision about 7.5 to 8 cm in length as shown and positioned in FIG. 4. Depending on the reamer size and shape, it is understood that it is also possible to pass the reaming blades through smaller portals less than 7.5 cm, less than 5 cm, less than 3 cm or less than 1 cm in length.

In embodiments that repair the humeral head first, a concave humeral head reaming blade is inserted thru the anterior-superior portal and attached to the reaming rod. The humerus articular surface is reamed and smoothed down to bleeding subchondral bone by reaming and pulling lateral on the threaded rod to a depth limited by a limit marker on rim of blade, as limited by the sleeve or as otherwise determined by the surgeon.

Figure 5A:
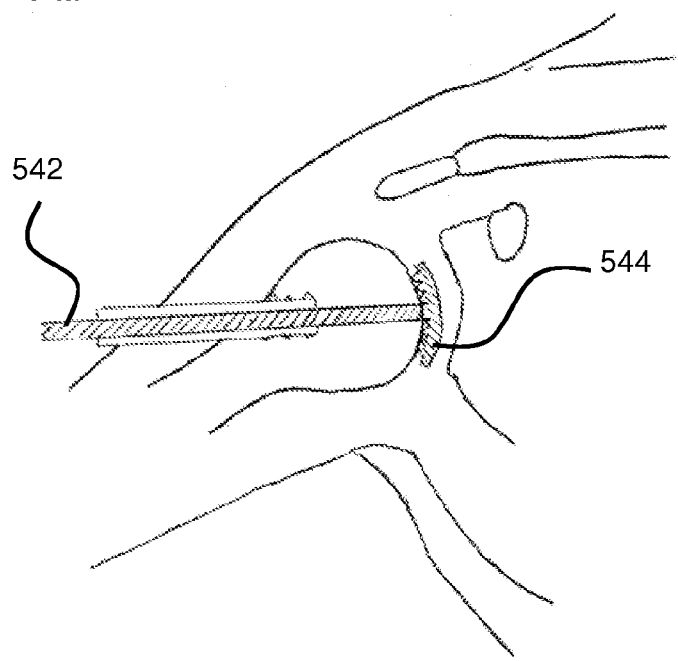
FIG. 5A illustrates the use of one example embodiment of a reaming rod and reaming blade for reaming the humeral head articulating surface.
Figure 5B:
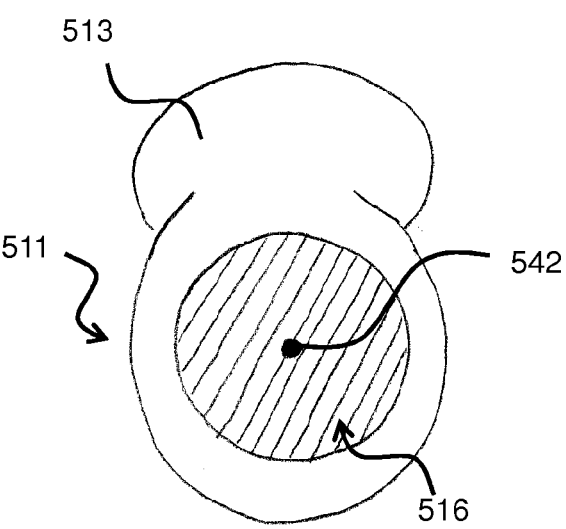
FIG. 5B illustrates a view of one example embodiment of the humeral head articulating surface from the medial side highlighting the reamed surface.

FIG. 5A shows a configuration of one embodiment of the reaming rod 542 and reaming blade 544 for this surface reaming. The reaming surface of the blade 544 is positioned against the articular surface and a reamer (not shown) is placed on the opposite end of the reaming rod 542 to turn the reaming blade 544 therefore reaming the articular surface. As shown, to accommodate the concave surface of the humeral head, the reaming surface of the blade is concave and a retrograde force is put on the reamer, the reaming rod 542 and the reaming blade 544. FIG. 5B illustrates shows a view of the reamed surface 516 of the humerus articular surface. This view shows the greater tuberosity 513 of the humerus, the humerus head 511, the reamed surface 516 and the threaded end of the reaming rod 542 in the bone tunnel.

The reaming rod and its connection to the reaming blade may be similar to those connection means described herein. For illustration, and not for limitation, an example connecting means between the reaming rod and the reaming blade is detailed in a cut-away view in FIG. 6A. This cut-away example includes a threaded female portion, or collar, as the connecting portion 645 for a reaming blade 644 that is connected with a threaded male portion 641 of the reaming rod 642. The threads are configured so that they do not loosen when turning to ream the surface. Once mated, the reaming rod may be turned which turns the reaming blade against the glenoid surface and reams the surface.

FIGS. 6B-6F show different views of example embodiments of the humerus reaming blade.

As shown in a top view of FIG. 6B, the reaming blade may have an elongated shape so that it creates a small profile when passing through the anterior-superior or other access portal. Suitable sizes include dimensions with a width W of about 10 to 20 mm, or about 15 mm in width, and a length L about 10 to 60 mm or about 40 to 56 mm in length. It is also suitable to have multiple length reamers for different surfaces and these can typically can be selected with length differences at about 5 mm increments. The reaming blade is made from a rigid surgical material such as, but not limited to titanium, stainless steel, or a cobalt-chrome alloy. The thickness of the blade is dependent upon the material it is composed of and as an example, the thickness may be about 1 to 5 mm or about 1 to 3 mm. As shown in FIG. 6C, the reaming blade in this embodiment has a reaming surface that is intended to generally correspond with the humeral articular surface and the bottom of a humeral head implant. Embodiments of the reaming blade reaming surface may have a generally curved shape consistent with the curves of common humeral surface reaming blades. As shown in FIG. 6C, this shape may correspond to a shape consistent with a central height CH of the reaming surface of about 5 to 40 mm or about 10 to 30 mm or about 15 to 24 mm. Blades may have a reaming surface with an axial radius AR, from an axial center of the blade to a blade edge at the edge of the reaming surface, consistent with the ranges of reaming blade length described above or about 5 to 30 mm or about 20 to 28 mm. As an illustrative example only, the radius of curvature at the central height may range from about 10 to 50 mm or from about 15 to 30 mm and the radius of curvature at the periphery may have a similar range. In some embodiments, the reaming surface may be more anatomic by having a larger radius of curvature at the periphery of the reaming blade than at its center. Other curvatures as may conform to the curvature of the joint surface being reamed are also suitable.

As shown in FIG. 6C, the reaming surface has multiple protrusions 649, preferably sharp, that frictionally engage the joint surface and remove a portion of the surface. Preferably, the protrusions are configured in a pattern that results in an even reamed surface. As shown, a suitable configuration is a "saw tooth" pattern with sharp protrusions 649 extending across and from the surface of the blade that when rotated scraps an even portion of articular cartilage and bone off the joint surface.

In some embodiments, the blade also includes depth limiting means that help ensure the reaming does not go beyond a certain depth relative to the surrounding joint surface. As shown in FIG. 6C, one embodiment of the depth limiting means are extended limiting tabs 648 that limits the depth of reaming by providing a surface that slides over a portion of the joint surface that is not be reamed. The surface of the limiting tab 648 is smooth compared to the portion of the surface that performs the reaming. The difference in height between the tip of the protrusions and the limiting tab defines the depth that the reaming will be performed before being limited by the tab. The tab surface can be enhanced with a reduced friction surface, such as a nylon or silicon that helps ensure the tab surface does not "ream" the surface. Another depth limiting means include calibrated markings on the side or rim of the reaming blade that function as limit markers and indicate the depth that the reaming surface of the blade is relative to the joint surface.

Additional alternative embodiments of the reaming blade are shown in FIGS. 6D-6F. These embodiments are shaped with dimensions similar to those described above such that they will provide a similar reamed surface to those illustrated and described for FIGS. 6A-6C. FIG. 6D shows an embodiment of a reaming blade 644 that is cross shaped with protrusions 649, here blades, extending from the reaming surface on the bottom surface of the reaming blade. FIG. 6E shows another embodiment of a circular reaming blade 644 that has protrusions 649, here multiple cutting teeth, extending from the bottom surface of the reaming blade to ream the joint surface. FIG. 6F shows another embodiment of a reaming blade 644 with protrusions 649, here teeth, extending from an exterior ring of the reaming blade as well as teeth extending from a cross bar that also has the reaming blade connecting portion.

Figure 7A:
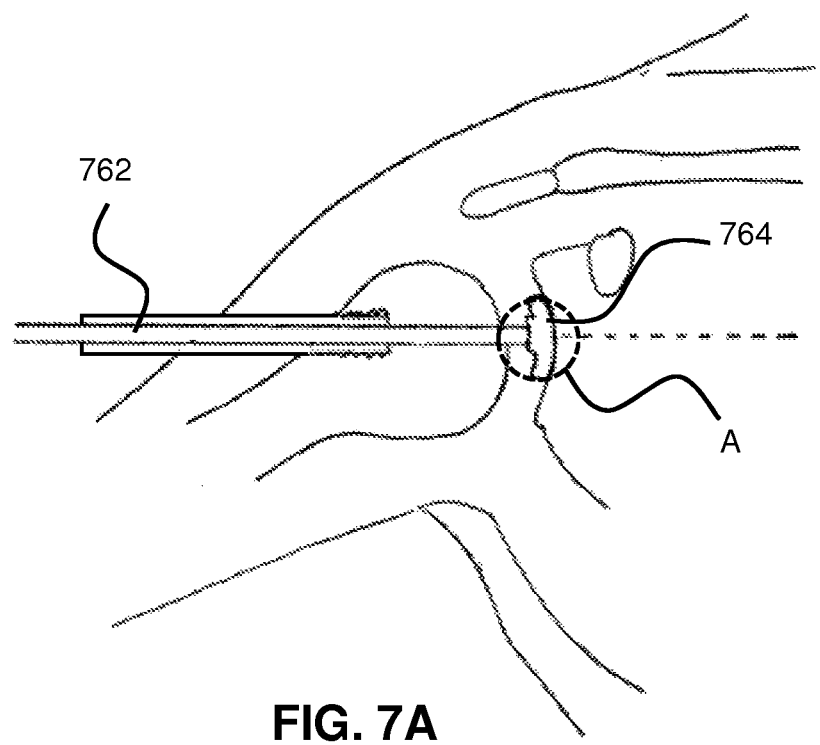
FIG. 7A illustrates the use of one example embodiment of a reaming rod and reaming blade for reaming the glenoid surface.

The methods describe may be performed on the shoulder joints in any order. For illustration of those embodiments that include repairing multiple joint surfaces, the methods and systems will be described as adding a second, or glenoid surface, to the first humerus surfaced described above. As shown in FIG. 7A, the second joint surface to be repaired in this example is the glenoid joint surface.

In some embodiments for multiple joint surfaces, the surface opposite the bone tunnel may have a guide hole drilled to help guide the positioning of the second reaming blade. This guide hole may be used to fit an element such as a central nipple from the reaming blade to guide and steady the reaming blade when reaming.

Referring again to FIG. 7A, to prepare this concave surface, a convex glenoid reaming blade 764 is passed thru the anterior-superior portal and held in a position between the humeral and glenoid surfaces as the connecting portion of the reaming rod 762 is attached to the connecting portion of the reaming blade. The reaming rod normally is the same as used for the reaming of the first surface, but need not be.

The means to connect the reaming rod and the reaming blade may be similar to those discussed above for the concave reaming blade. For illustration, and not for limitation, an example connecting means between the reaming rod and the reaming blade is detailed in a cut-away view for A of FIG. 7A in FIG. 8A. This cut-away example includes a threaded female portion, or collar, as the connecting portion 865 for a reaming blade that is connected with a threaded male portion 861 of the reaming rod. The threads are configured so that they do not loosen when turning to ream the surface. Once mated, the reaming rod may be turned which turns the reaming blade against the glenoid surface and reams the surface.

Figure 8A:
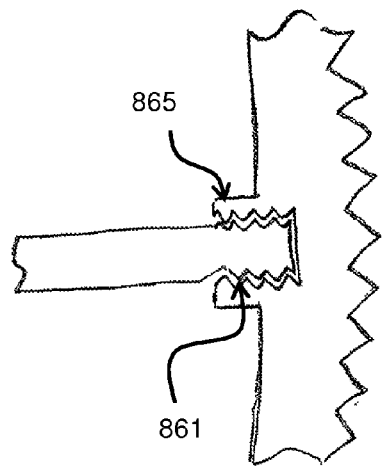
FIG. 8A illustrates a cut away side view of the embodiment of the reaming rod and reaming blade from section A of FIG. 7A showing details of their connecting means.
Figure 8E:
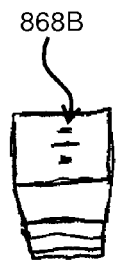
FIG. 8E illustrates one example embodiment of a limit marker on the side of the reaming blade to identify a reaming limit.
Figure 8B:
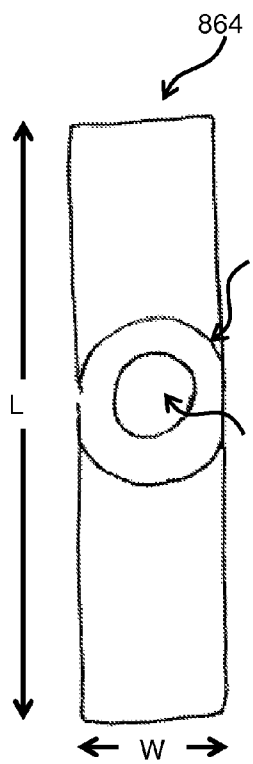
FIGS. 8B-8D illustrates bottom, top and side views respectively of the reaming blade of FIG. 8A.
Figure 8C:
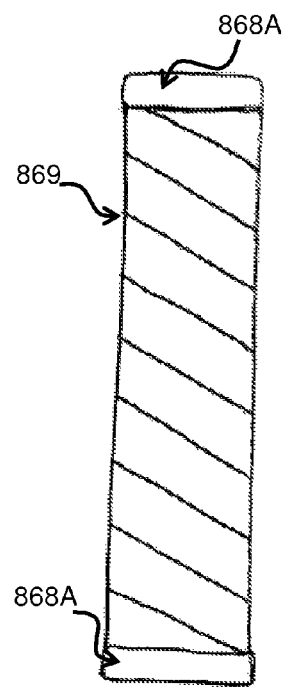
Figure 8D:
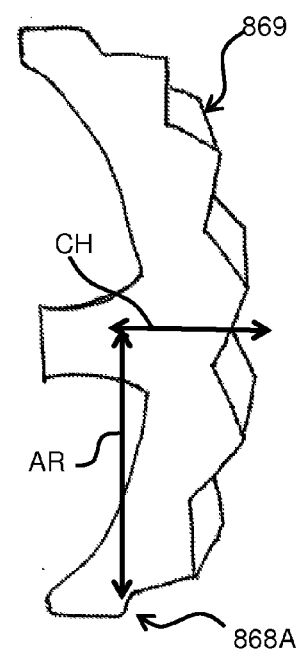

As can be seen in FIGS. 8B-8D, the design of this reaming blade 864 has some similar elements as the reaming blade features described earlier with the connecting portion 865, protrusions 869 and an optional limiting tab 868A. For a concave surface, as is illustrated here, the blade has a convex reaming surface. In some embodiments, a centered nipple may also extend from the top, coronal surface of the convex reaming blade.

As shown in a bottom view of FIG. 8B, this reaming blade embodiment has an elongated shape so that it creates a small profile when passing through the anterior-superior or other access portal. Suitable sizes include dimensions with a width W of about 10 to 20 mm or about 15 mm, and a length L of about 10 to 60 mm or about 40 to 56 mm. It is also suitable to have multiple length reamers for different surfaces and these can typically can be selected with length differences at about 5 mm increments. The reaming blade is made from a rigid surgical material such as, but not limited to titanium, stainless steel, or a cobalt-chrome alloy. The thickness of the blade is dependent upon the material is it composed of and as an example, the thickness may be about 1 to 5 mm or about 1 to 3 mm. As shown in FIGS. 8C and 8D, the reaming surface has multiple protrusions 869, preferably sharp, that frictionally engage the joint surface and remove a portion of the surface. Preferably, the protrusions are configured in a pattern that results in an evenly reamed joint surface. As shown, a suitable configuration is a "saw tooth" pattern with sharp protrusions 869 extending across and from the surface of the blade that when rotated scraps an even portion of articular cartilage and bone off the joint surface. Embodiments of the convex reaming blade may generally have a larger radius of curvature than the concave humerus reaming surface so that it more closely accommodates the curvature of the glenoid and its implants. As shown in FIG. 8D, the shape of the reaming blade reaming surface may correspond to a shape consistent with a central height CH of about 5 to 40 mm or about 10 to 30 mm or about 15 to 24 mm. Blades may have an axial radius AR, from an axial center of the blade to a blade edge at the edge of the reaming surface, consistent with the ranges of reaming blade length described above or about 5 to 30 mm or about 20 to 28 mm. As an illustrative example only, the coronal radius of curvature at the central height CH may range from about 10 to 50 mm or from about 15 to 30 mm and the radius of curvature at the periphery may have a similar range. The radius of curvature of this reaming blade surface matches that of the non-articular side of the glenoid implant. Other curvatures as may conform to the curvature of the implant are also suitable. In some embodiments, the blade also includes depth limiting means that help ensure the reaming does not go beyond a certain depth relative to the surrounding joint surface. As shown in FIG. 8D, one embodiment of the depth limiting means are limiting tabs 868A that limits the depth of reaming by providing a surface that slides over the joint surface similar to the limiting tabs described for the reaming blade in FIG. 6C. As shown in FIG. 8E, another depth limiting means include calibrated markings 868B as the limit markers on the side or rim of the reaming blade that indicate the depth that the reaming surface of the blade is relative to the joint surface.

Figure 9A:
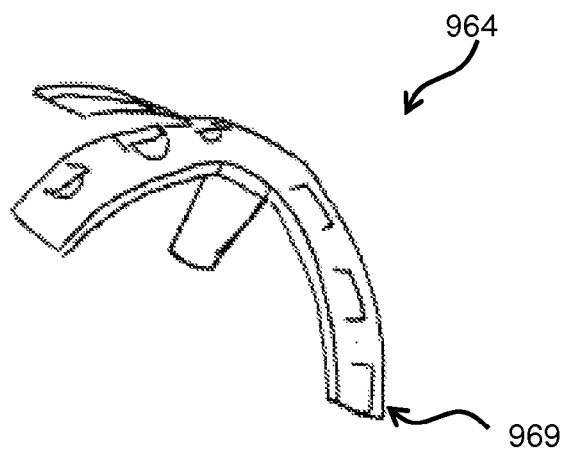
FIGS. 9A-9C illustrate example embodiments of glenoid reaming blades for convex surfaces.
Figure 9B:
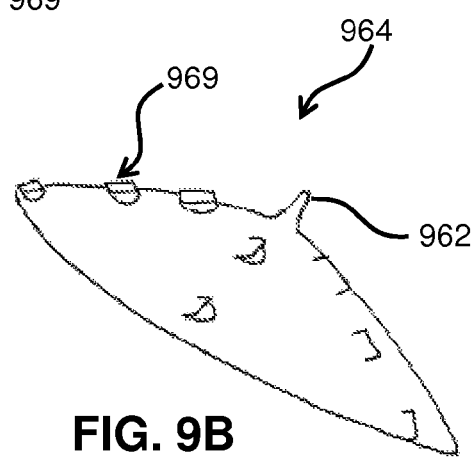
Figure 9C:
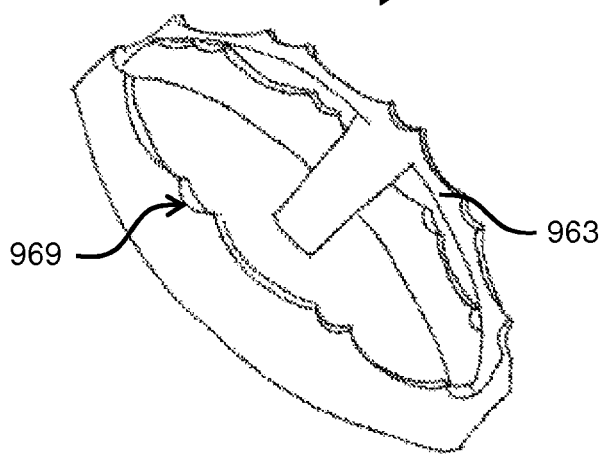

Alternative embodiments of reaming blades shaped to ream concave surfaces are shown in FIGS. 9A-9C. The reaming surface may be any type of surface configured to evenly ream a concave surface when rotated and with a force applied in the direction of the reaming surface.

FIG. 9A illustrates a top perspective view of one embodiment of an X-shape reaming blade 964 with the reaming surface on the top surface. Illustrated here is a reaming surface comprising a series of patterned notches with protrusions 969, here protruding blades, configured to evenly ream a concave surface.

FIG. 9B illustrates a top perspective view of one embodiment of a circular shaped reaming blade 964 with the reaming surface on the top surface. Illustrated is a reaming surface comprising a series of patterned notches with protrusions 969 configured to evenly ream a concave surface. Also shown in this embodiment is a protruding nipple 962 to be received in a guide hole to help stabilize the reaming blade when reaming the joint surface.

FIG. 9C illustrates a top perspective view of one embodiment of a ring shaped reaming blade 964 with a cross member 963. The reaming surface on the top surface of both elements and comprising a series of protrusions 969, here notches, configured to evenly ream a concave surface.

With the reaming blade connected to one end of the reaming rod, the other end of the reaming rod is connected to a reamer. Using the reamer, such as a battery powered reamer, the glenoid is smoothed and reamed down to the subchondral bleeding bone. The depth of the reaming may be limited by the depth limiting means on the reaming blade. The depth may also be limited by other means. For example, and not for limitation, the reaming rod may have calibration marks along its outside surface whereby when the rod is in the sleeve in the bone tunnel, the surgeon can limit reaming depth by limiting movement of the rod, as measured by movement of the calibration marks against the end of the sleeve, to the depth of reaming desired. Laser provided marks can serve as suitable calibration marks on the rod.

Figure 7B:
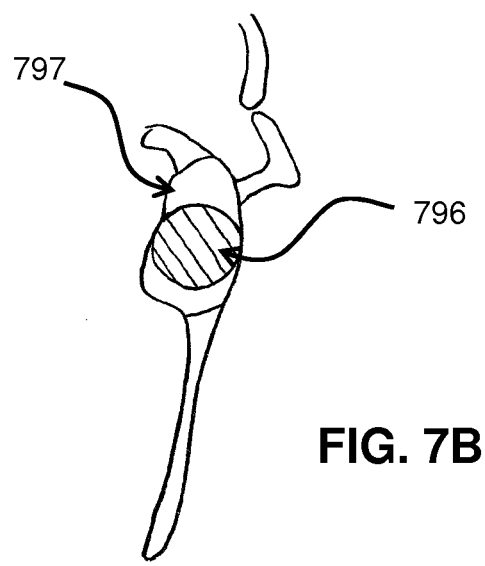
FIG. 7B illustrates a view of one example embodiment of the glenoid surface from the lateral side highlighting the reamed surface.

With the second joint surface reamed, the reaming rod, reaming blade and other glenoid reaming instruments can now be removed. FIG. 7B shows a side view of the resulting round reamed surface 796 of the glenoid surface 797.

Figure 10A:
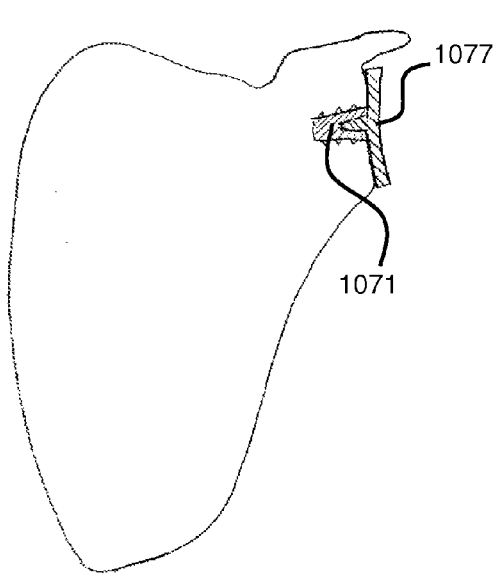
FIGS. 10A-10D illustrate example embodiments of glenoid anchors and implants as implanted.
Figure 10B:
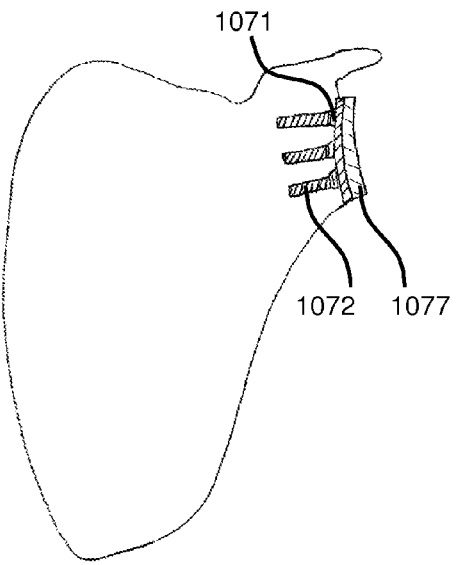

In some embodiments, anchors for implants that require anchors can be set at this stage of the method. For those embodiments, pilot holes can be drilled and tapped through the bone tunnel with or without a guide wire. An example of this type of anchor setting is shown in FIG. 10A where a pilot hole is drilled and the fixation element 1071, such as threaded screw with morse tapered system, is set into place. The pilot may be any suitable size, in one embodiment the pilot hole is 4.0 mm. FIG. 10B shows an example implant system utilizing one or more screws 1072 that secure an implant anchor 1071. The screws may be cancellous locking screws. With the anchors set, all glenoid reaming instruments can now be removed and the anchors 1071 can be used to secure a polyethylene, plastic, ceramic material or metal glenoid surface implant 1077. It is also understood that the implants may be directly anchored into the joint.

For implants having multiple pegs, multiple tunnels can be reamed through multiple steps of (1) positioning the tunnel through the humerus so that its axis aligns with the desired peg placement and (2) drilling or tapping through the tunnel into the glenoid surface to create tunnels or pilot holes for the implant pegs. In some embodiments, the tunnel may be reamed over a guide wire. In some embodiments, the humerus may need to be moved in any direction to allow for implant pegs that are positioned parallel to each other. In some embodiments with three pegs, the pegs and the tunnels are placed central, central inferior and central superior on the glenoid surface. Embodiments with more than three pegs, most likely five pegs, are also anticipated.

After irrigating all debris from the joint, and removing the reaming instruments, the implants can be secured. For cemented connections, the irrigation may be stopped and the joint may be given an opportunity to dry.

Although any shape is suitable, glenoid implants will typically be oval shaped and will be selected based on the geometry of the glenoid. The glenoid implants may be sized by the surgeon during the surgery or they may be determined during the preoperative procedures described herein.

Once selected, the glenoid implant is placed into the joint thru the anterior-superior portal and positioned over the anchor or anchor locations. For the anchor shown in FIG. 10A, the implant is positioned over the threaded screw in the glenoid and impacted in place with the morse tapered attachment on the implant using an impactor, for example a 4.5 mm impactor, through the lateral sleeve.

For the anchor type shown in FIG. 10B, the implant is positioned over the anchor and is either cemented into place or secured into place using a coupling or engagement of retaining elements of the anchor with the retaining elements of the implant.

Figure 10C:
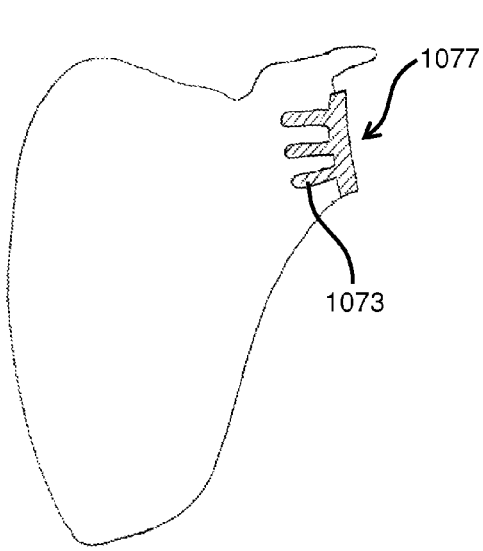

FIG. 10C shows an example "inlay" design implant that is impacted or cemented into place and having polyethylene, plastic, ceramic material or metal glenoid surface implant 1077 with pegs 1073 cemented into the bone.

Figure 10D:
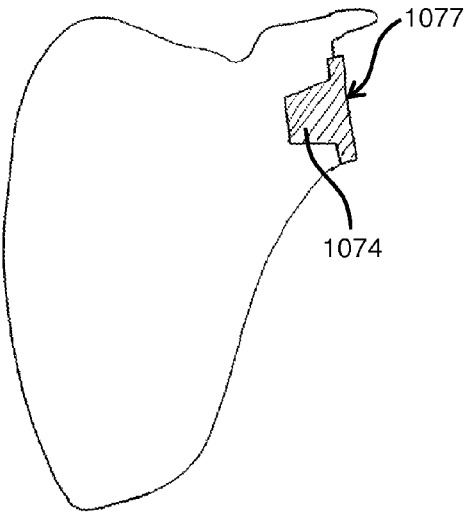

FIG. 10D shows another example implant that is impacted into place having a polyethylene, plastic, ceramic material or metal glenoid surface implant 1077 and keel 1074 cemented into the bone.

With the glenoid implant completed, the humerus implant may then be placed through the portal and secured to the humeral head using orthopedic securing means for implants such as adhesives, cement, friction or mechanical means.

In some embodiments, the implants are coated with an ingrowth material as described herein that may enhanced bone in-growth into the implant. Some embodiments prefer the circumference of the implant or the implant surface to be contained in cortical bone. In some embodiments, the use of multiple pegs and/or the in-growth material on the underside of the implant allows the implant to be secured within the bone without having to have the circumference of the implant surface contained by cortical bone.

In one embodiment, the means to secure may be provided by the configuration and cooperation of the implant, a stem and a fixation element. In the embodiment shown in FIG. 11A, the humerus implant 1131 has a collar configured to connect with a stem implant end of the stem 1135. The connections that may be used include any type of mating connection such as threaded, friction, push pin, clipped or pinned connections that can be connected and/or disconnected in a confined space. In this embodiment, the collar is a threaded collar 1133 on the underside of the implant that may be attached to a stem implant end that is threaded. The stem 1135 has another stem fixation element end that is used to connect or engage with an end of the fixation element 1120. In this case, the stem fixation element end of the stem has an engaging surface, such as an internal bore 1137 with threads or other protrusions to engage the engaging surface of the fixation element 1120, such as external threads. As shown, the fixation element 1120 has a fixation element stem end and a fixation element head end, or proximal end. In this embodiment, the fixation element stem end 1128 is threaded to be engaged by and advanced into the stem bore 1137. The fixation element proximal end 1122 may also be shaped to be engaged by an anchor tool such as a wrench or screwdriver allowing the fixation element to be turned so that it engages the stem. The diameter of the fixation element proximal end may be sized to restrict the movement of the fixation element at some point so that the fixation element proximal end provides the anchoring surface to anchor the stem 1135 and the implant 1131. As shown, the lateral humerus cortex may be counter sunk and the fixation element proximal end fits within the counter sunk diameter but not the step created by the smaller bone tunnel diameter. With this step, when the fixation element is mated with the stem and the fixation element proximal end is restricted by the bone tunnel step, the fixation element proximal end provides the anchoring surface against the step so that the fixation element 1120 secures the humeral resurfacing implant 1131. As illustrated in this embodiment, the fixation element 1120 may be accessed from an opposite or proximal end of the bone tunnel, opposite the implant end, to anchor and secure the stem and implant in the bone tunnel.

Figure 11A:
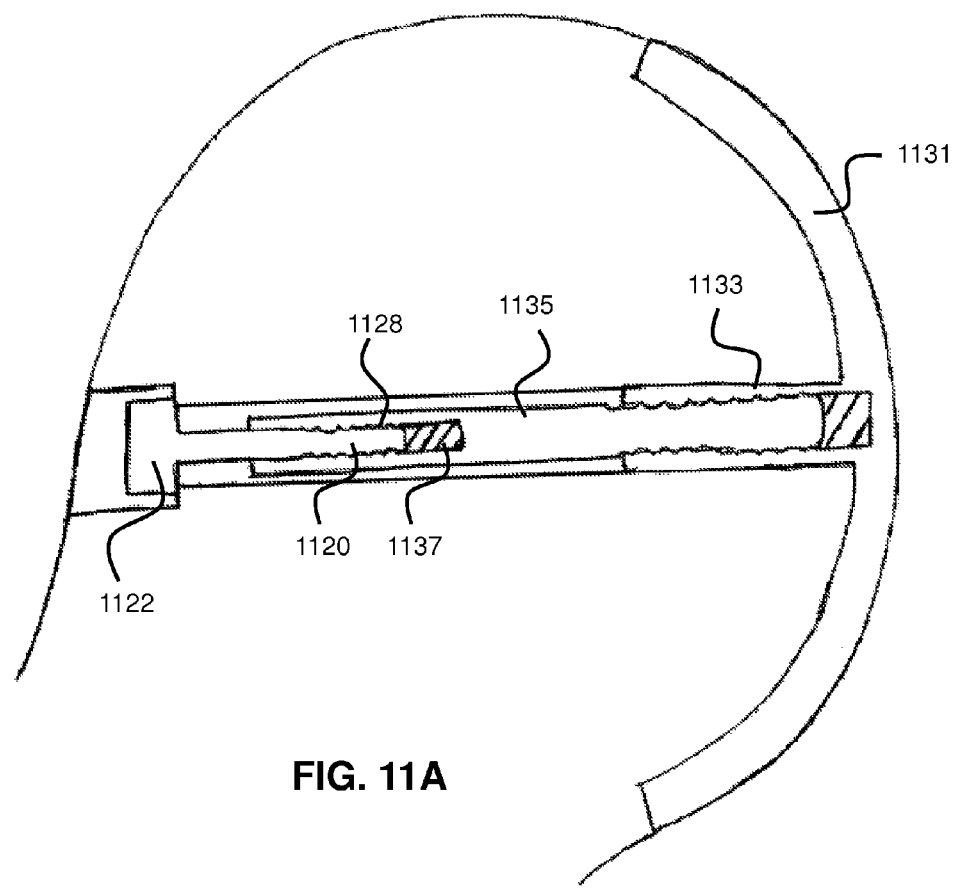
FIG. 11A is a cut away side view of one example embodiment of an implant, stem and a fixation element illustrating them anchored in a bone tunnel.

Given the example embodiment of FIG. 11A, the anchor is implanted by positioning the implant, inserting the stem through the bone tunnel from the proximal end of the tunnel, ensuring the stem is secured to the implant, inserting the fixation element from its tunnel proximal end and engaging the stem with the fixation element whereby the fixation element anchors the implant on the joint surface. Similar methods may be applied to other embodiments of the stem, fixation element and implant.

After the fixation element, stem and implant are secured, the sleeve may be removed.

Alternative embodiments of transosseous fixation elements and stems are shown in FIG. 12A-12D.

Figure 12A:
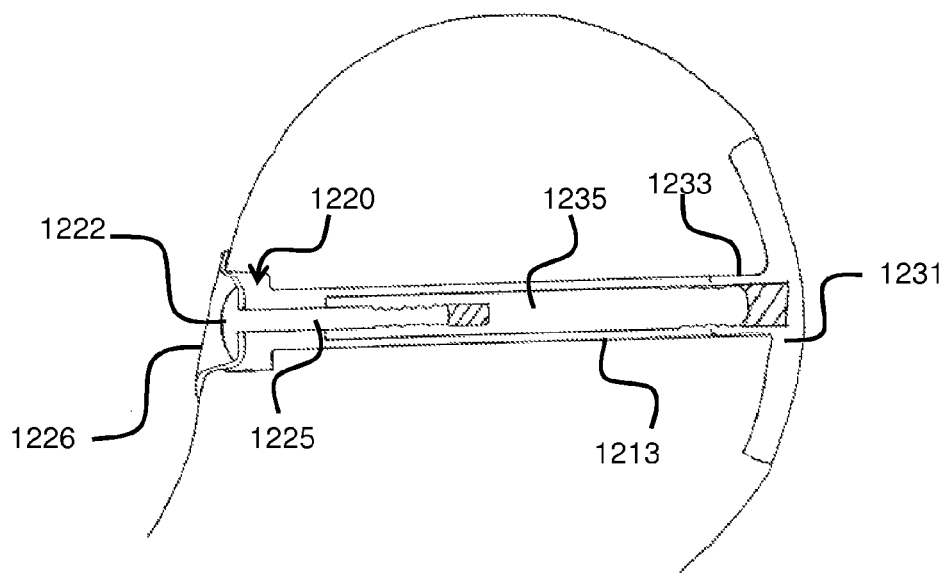
FIG. 12A is a cut away side view of another example embodiment of an implant, stem and fixation element illustrating them anchored in a bone tunnel.

Another embodiment of the implant, stem and fixation element is shown in FIG. 12A. In this embodiment, the fixation element 1220 may be a bolt and washer type element with the washer portion 1226 having a bore to receive the bolt portion 1225 but retained by a head 1222 on the proximal end of the fixation element 1220. The implant end of the stem 1235 engages the implant collar 1233 with mating threads so that a turning of the stem proximal end advances the stem 1235 and tightens the implant in the implant collar 1233. Tightening the head 1222 and the bolt portion 1225 of the fixation element 1220 engages the washer portion 1226 and provides the anchoring surface for the implant. In this embodiment, the washer portion 1226 has an indented shape towards its center so that the periphery of the washer portion 1226 rests against the lateral humerus cortex and the center of the washer provides a surface flat for the head 1222 of the fixation element. This embodiment allows the implant system to be anchored without having to counter sink as much of the proximal end of the fixation element in the bone tunnel 1213.

It is also understood that embodiments of the fixation element and the stem, as well as the implant and the stem may be integrated into single elements that perform the function of the two elements. For example, referring to the embodiment of FIG. 12A, the bolt portion 1225 of the fixation element 1220 can be integrated with the stem 1235 to create a single connecting element to the implant 1231 and the washer portion 1226.

Figure 12B:
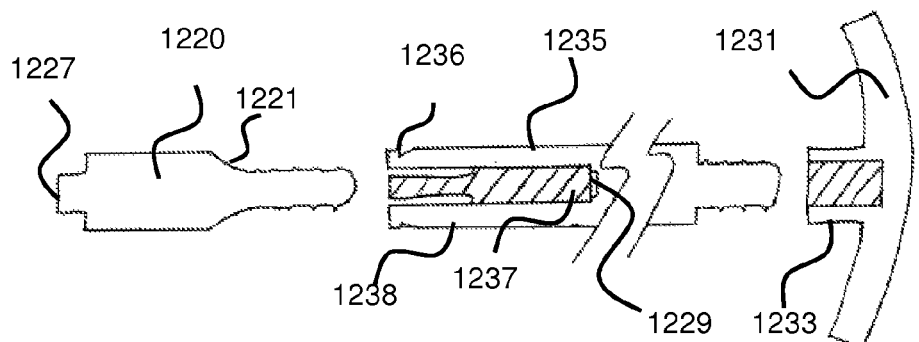
FIG. 12B is a cut away side exploded view of another example embodiment of an implant, stem and fixation element.

Another embodiment of the implant, stem and fixation element is shown in FIG. 12B. In this embodiment, the implant end of the stem 1235 is connected to the implant collar 1233 with male threads on the stem and a female threaded recess on the implant collar. This connection may be made with a tool engaging element 1229 that allows a tool to insert the stem through the bone tunnel and rotate it into the collar threads. The tool may be similar to a screw driver or wrench with a head that engages a tool engaging element 1229, like a mating indent in a bore of the stem similar to the indent in the head of a screw or bolt. The neck of the tool may be received in a bore of the stem to help position and guide the stem through the bone tunnel. The stem fixation element end of the stem 1235, opposite the implant end, is shaped to connect to an end of the fixation element 1220. As shown, the connection of the stem and fixation element is shaped so that fingers 1238 of the stem 1235 expand into the bone tunnel and against the walls of the bone tunnel as the fixation element 1220 advances into the stem 1235. The advancing of the fixation element 1220 is assisted by a bore 1237 that is fitted to the diameter of fixation element 1220. The expansion is provided by the bore 1237 that is expanded by a ridge 1221 on the fixation element 1220 that has a tapered outer periphery that gets larger in relation to the bore 1237 as the fixation element 1220 advances into the bore 1237. The expansion of the fingers 1238 increases the diameter of the stem outer surface against the inner surface walls of the bone tunnel and engages the bone and provides the anchoring surface for the stem 1235 to anchor the stem in the bone. Protrusions 1236 or other frictionally enhanced surface elements on the outer surface of the stem fixation element end may assist in the anchoring the stem 1235 in the bone tunnel. The proximal end of the fixation element 1220 may also have a tool engaging element 1227 that provides a connection to a tool so that the fixation element 1220 can be positioned in the bone tunnel and turned to secure it in the stem. This embodiment allows the implant 1231 to be anchored in the tunnel with less concern about the overall length of the stem and fixation element because the fixation element proximal end does not have to be proximal to the surface of the lateral cortex to provide the anchoring surface.

Figure 11B:
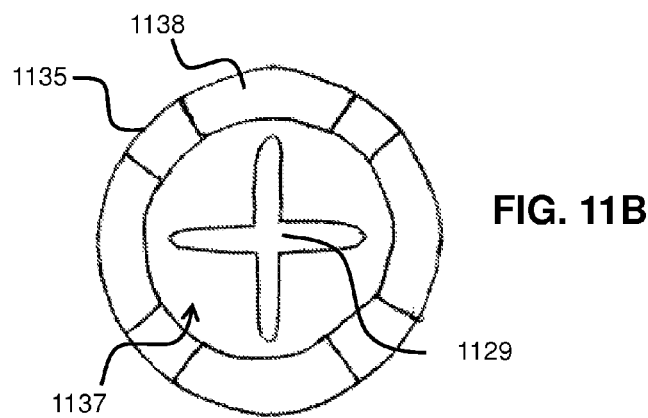
FIG. 11B is an end view of one example embodiment of a stem from the stem fixation element end.

FIG. 11B illustrates one example embodiment of the tool engaging element 1129, in the bore 1137 of the stem 1135. Viewing the stem 1135 with fingers 1138 from the stem fixation element end, shown is a recess, like the head of a screw, as the tool engaging element 1129.

Figure 12C:
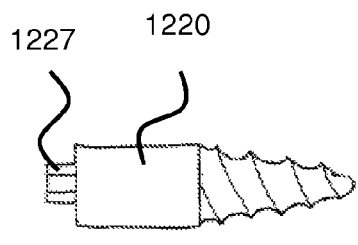
FIG. 12C is a side view of another example embodiment of a fixation element.

In another embodiment of the implant system, the fixation element may be shaped as shown in FIG. 12C. This embodiment functions similar to the embodiment of FIG. 12B, but the connecting element, here threads, of the fixation element 1220 are more aggressive and engage the stem bore 1237 (see FIG. 12B) without the need for the fitted connection section of the fixation element and stem bore. Similar to FIG. 12B, the advancing of the fixation element 1220 expands the fingers of the stem into the bone tunnel wall anchoring the stem and the implant.

Figure 12D:
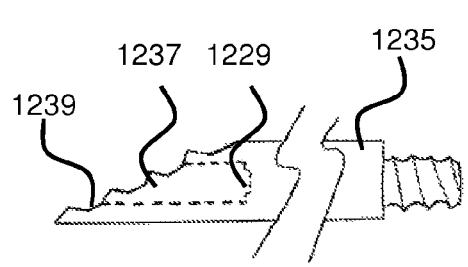
FIG. 12D is a side view of another example embodiment of a stem.

In another embodiment of the implant system, the stem may be shaped as shown in FIG. 12D. This embodiment functions similar to the embodiments of FIGS. 12B and 12C, but the stem 1235 does not have a bore to receive the fixation element 1220 (see FIG. 12C). The stem 1235 has a slanted surface 1239 that together with the inner wall of the bone tunnel define the bore to receive the threaded end of the fixation element 1220. This embodiment of the stem 1235 illustrates an internal bore 1237 to accept the positioning tools to connect the stem 1235 to the implant 1231 (see FIG. 12B). One benefit of this embodiment is that the fixation element may be similar to a bone anchor used to secure ligaments in bone.

Example implants also include embodiment similar to those disclosed in U.S. Pat. No. 7,604,641 entitled "SYSTEM AND METHOD FOR JOINT RESURFACE REPAIR" to Tallarida et. al., filed Apr. 18, 2006 ("Tallarida") which is herein incorporated by reference in its entirety as well as those implants advertised by Arthosurface at 28 Forge Parkway in Franklin Mass. For use with the elements described herein, elements, such as the stem and the implant or implant anchor may be modified to engage the fixation elements described. Having an implant stem with means to engage the fixation element allows the implant to be secured from the bone tunnel end opposite the implant. For example, the implants and cannulated posts can be modified to include the posts mated with the fixation elements described herein. Additionally, the implants can be mated with the stems and fixation elements described herein to provide alternative anchoring systems that utilize the features of transosseous bone tunnels and can be utilized with the minimally invasive methods described herein.

Figure 13:
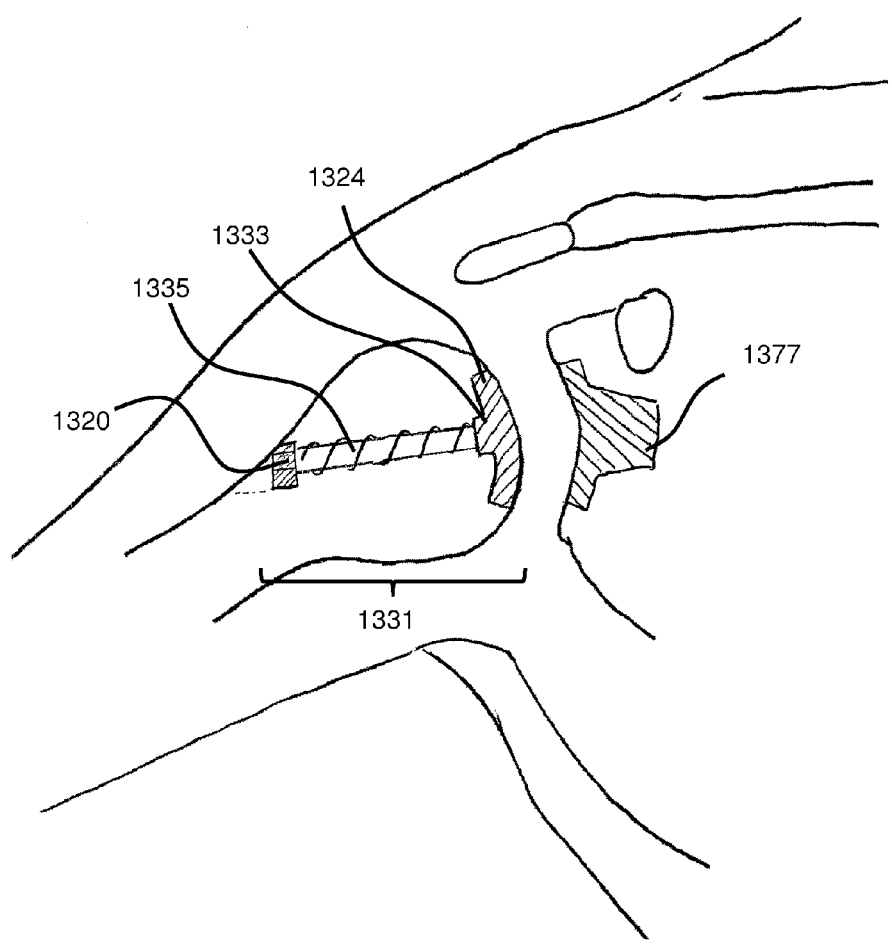
FIG. 13 is an anterior view of a joint illustrating one example embodiment of multiple implants secured using the methods and systems disclosed.

FIG. 13 illustrates one embodiment of implants secured on both surfaces of a typical shoulder joint showing the humerus implant 1331 comprising the humeral head implant 1324 with the threaded collar 1333, the stem 1335, the fixation element 1320 and the glenoid implant 1377. For example only, and not for limitation, a 4.5 mm threaded rod may be used as the fixation element that threads into the collar of the implant as the stem, and the lateral humerus cortex can be counter sunk about 2 mm using about a 6 mm cannulated reamer.

Figure 14:
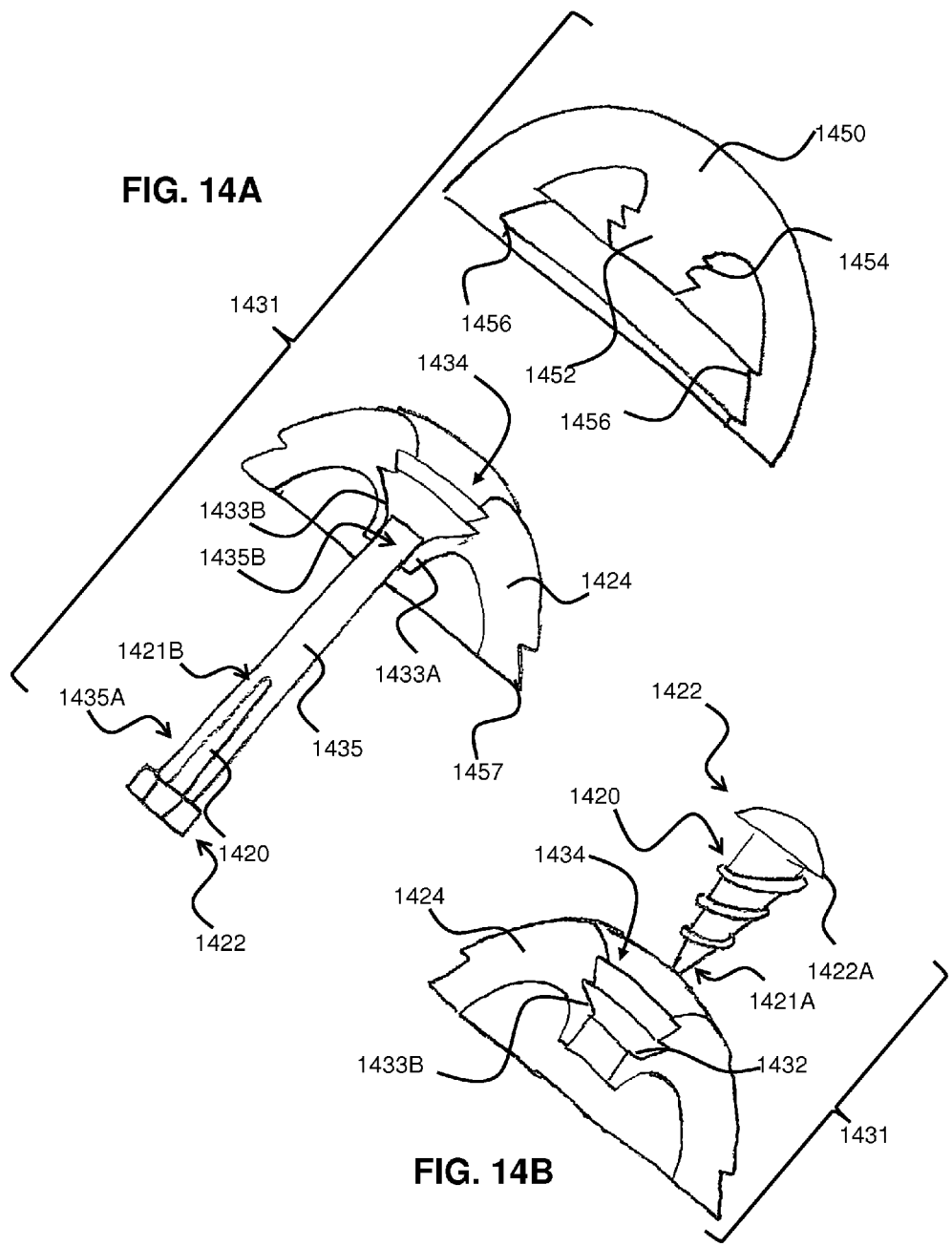
FIG. 14A illustrates a side cut-away view of one example of an embodiment of a humeral implant having an implant anchor a surface cap.
FIG. 14B illustrates a side cut-away view of one example of an embodiment of a humeral implant having an implant anchor and a surface cap.
Figure 15:
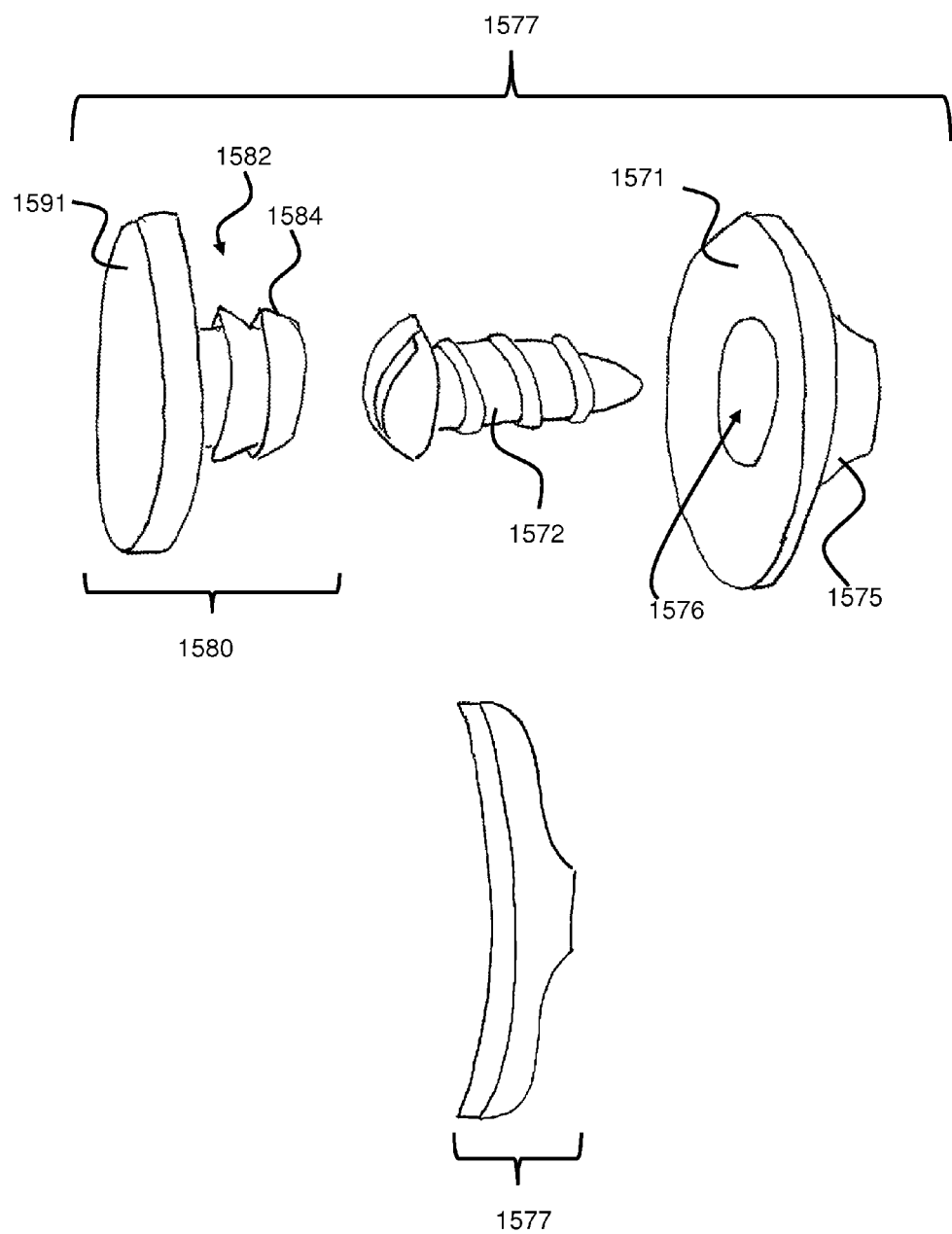
FIG. 15 illustrates side views of an example of an embodiment of a glenoid implant having an implant anchor and a surface cap.

Embodiments of the above implants may comprise an implant system having multiple elements and these elements may be made from different types of materials. For example, some embodiments may have an implant comprising an implant anchor and an implant surface cap. Some embodiments may have a surface cap made of a particular material which covers the implant anchor made of another material. In these embodiments, the implant system may generally comprise a implant anchor having a anchor retaining element, a implant surface cap with a cap retaining element and the cap retaining element is configured to couple with the anchor retaining element whereby the implant surface cap is coupled to the implant anchor. In some embodiments, the method of securing the implant surface cap to the implant anchor through the underside of the surface cap, allows the joint surface of the implant surface cap, the articulating surface interacting with the other joint surface of the joint, to be free from any elements connecting the cap to the implant. For illustration purposes only, FIGS. 14A-14B and 15 illustrate example embodiments of implants with a surface cap configured to cover an implant anchor. Each of these implants may be used with a second implant or second implant system having a surface cap or they may be used with an implant made of single material such as a metal implant. Although these implant systems are described as being used for humeral and glenoid implants, it is understood that they may be used as implant for many different joints.

As shown in FIG. 14A, one embodiment of a humerus implant system 1431 comprises the implant anchor 1424, the implant surface cap 1450 with the cap collar 1452, the stem 1435 and the fixation element 1420. In this embodiment, the humeral implant anchor 1424 also comprises an anchor collar 1433B defining a bore 1434 to receive portions of the cap 1450 and at least one retaining element 1432 to provide a securing point to couple and secure the surface cap 1450 in the bore 1434. The implant surface cap 1450 is shaped to fit over and be secured in the implant anchor 1424. The implant surface cap 1450 has an outer surface which generally creates the articulating surface for the implant anchor 1424 and engages the articulating surface of the glenoid or the glenoid implant. The implant surface cap 1450 may also have a male collar 1452 with retaining elements 1454 to mate with retaining elements 1432 in the anchor collar 1433. The implant surface cap 1450 may also have at least one cap supplemental engaging elements 1456 to mate with at least one anchor supplemental engaging element 1457 on the implant to provide a supplemental securing point and further couple or secure the implant surface cap 1450 to the humeral implant anchor 1424. In this embodiment, the humeral implant anchor 1424 and the implant surface cap 1450 are secured into the bone with the stem 1435 and the fixation element 1420 as described above. In embodiments, the stem 1435 may have a fixation element end 1435A and an anchor end 1435B with the anchor end of the stem 1435 configured to mate with the implant anchor 1424 at an anchor collar 1433A utilizing any connection method such as those described herein. In embodiments, the fixation element may have a head end 1422 and a stem end 1421B configured to mate and couple with the fixation element end of the stem 1435 whereby when the fixation element 1420 is secured to a bone, the fixation element 1420 secures the stem 1435 and the implant anchor 1424 to the bone.

FIG. 14B illustrates another embodiment of a humerus implant system where the humeral implant anchor 1424 is secured in the bone with a fixation element 1420 which is received through the bore 1434 and secured into the bone. The fixation element 1420, on its head end 1422 may have has retaining elements 1422A, such as the bottom of the head, that engage retaining elements 1432 in the humeral anchor collar 1433B, such as a reduce bore diameter, to secure the fixation element 1420 to the humeral implant anchor 1424. The opposite end of the fixation element 1420 may comprise a fixation end 1421A configured to fix or otherwise anchor the fixation element 1420 in a bone. In this embodiment, the fixation element 1420 may comprise common anchoring element such as a bone screw or a bone in-growth screw.

These embodiments of a humeral implant system 1431 may be used with the glenoid implants described herein.

FIG. 15 illustrates another example embodiment of an implant having an implant anchor and a separate surface cap. In this embodiment, a glenoid implant 1577 comprises an anchor 1571, a retaining element 1572, a stem 1575 and a surface cap 1580 configured to be coupled to and cover the anchor 1571. The glenoid implant anchor 1571 further comprises a bore 1576 to receive the retaining element 1572 and receive a portion of the surface cap 1580. The bore 1576 also comprises internal retaining elements (not shown) to mate and couple with retaining elements of the surface cap 1580. The surface cap 1580 comprises a surface 1591 a collar 1582 and one or more retaining elements 1584. The glenoid implant 1577 is secured in the bone by securing the anchor 1571 in the bone with the retaining element 1572. The surface cap 1580 is secured to the anchor 1571 by the collar 1582 extending into the bore 1576 and the retaining elements 1584 mating with retaining elements of the surface cap 1580. These elements are configured so that when the glenoid implant anchor 1571 is secured into the bone and the surface cap 1580 is secured to the glenoid implant anchor 1571, the surface cap 1580 has an outer surface that generally creates the articulating surface for the glenoid implant 1577 and engages the articulating surface of the humerus or the humerus implant. The retaining element 1572 may be any element to secure the anchor to bone such as, but not limited to a bone in-growth screw, pegs or any other method of securing the anchor to the bone. FIG. 15 also illustrates a side view of the surface cap 1580 secured to the anchor 1571.

For embodiments with surface caps, methods of securing the implant anchor and surface cap to the bone may include securing the implant surface cap to the implant anchor at any step of the procedure deemed appropriate by the surgeon. For example, for embodiments of the implant system that are secured to a bone tunnel from the underside of the implant anchor, the surface cap may be secured to the implant anchor before or after positioning on the bone and securing to the bone. For embodiments that are secured to the bone through an access point on the surface side of the implant, the surface cap is generally secured to the implant anchor after securing the implant anchor to the bone.

In embodiments of implant systems with surface caps, the surface cap may be any type of material to provide a favorable surface to engage the other articulating surface. These surfaces may comprise a plastic, polyethylene, metal, ceramic, carbon or any composite of these materials. In some embodiments, the surface cap comprises Ultra-High Molecular Weight Polyethylene (UHMWPE), medical grade UHMWPE, crosslinked UHMWPE, highly crosslinked polyethylene (XLPE), thermally treated UHMWPE, UHMWPE infused with Vitamin E or UHMWPE reinforced with carbon nanotubes (CNT). The surface cap may also be high density carbon impregnated with specially treated polycarbonate. Materials used for single component implants, or for use with surface caps, may also include ceramics, metals, cobalt-chromes, metal/ceramic hybrid, any other surgical grade material or any combination of these materials.

Although example embodiments are shown with particular anchoring elements in FIGS. 14A-14B and 15, it is understood that the embodiments of FIGS. 14A-14B and 15 are also capable of using the anchoring systems described above and illustrated in the preceding FIGS. For example, these embodiments of implants with a surface cap may also be anchored in the bone by any of the methods described above such as but not limited to mating morse taper connections on the anchor and the retaining element. It is also understood that embodiments of the implants described above in FIGS. 10-13 may also utilize the implant anchor and implant surface cap embodiments described and illustrated in the examples of FIGS. 14A-14B and 15.

For the implant system elements that have surfaces against bone, typically under or peripheral surfaces, embodiments of the system elements may have surfaces that enhance bony ingrowth to help secure the elements after surgery. In particular, it may be helpful for the underside of implants, stems and fixation elements to contain a bony ingrowth material that allows the bone adjacent to the implant element to grow into the implant element aiding in the long-term fixation of the implant and implant elements. Ingrowth materials may include, but are not limited to autologous and allograft osteoprogenitor cells and tissues, bone-morphogenic proteins, hydroxyapaptic coating, trabecular metal, porous metal, porous metal coating and tantalum.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. Although this invention has been described in the above forms with a certain degree of particularity, it is understood that the present disclosure has been made only by way of example and numerous changes in the details of construction and combination and arrangement of parts may be resorted to without departing from the spirit and scope of the invention.

I claim:

1. A method of performing a joint repair, the method comprising the steps of:
    reaming a transosseous bone tunnel extending through a bone to a first joint surface;
    positioning a reaming rod through the bone tunnel after reaming the bone tunnel;
    connecting a first reaming blade to the reaming rod;
    reaming the first joint surface with the first reaming blade before inserting a stem of a first implant system in the bone tunnel;
    after reaming the first joint surface and before inserting the stem of the first implant system in the bone tunnel:
        removing the first reaming blade from the reaming rod,
        connecting a second reaming blade to the reaming rod,
        ensuring the bone tunnel is perpendicular to a second joint surface,
        reaming the second joint surface,
        removing the second reaming blade from the reaming rod,
        removing the reaming rod from the bone tunnel,
        placing a second implant anchor on the second joint surface, and
        securing the second implant anchor on the second joint surface;
    inserting the stem of the first implant system in the bone tunnel;
    positioning an implant anchor on the first joint surface;
    securing the stem to the implant anchor;
    securing an implant surface cap to the implant anchor; and
    anchoring the stem and the implant anchor to the bone from a proximal end of the bone tunnel.

2. The method of claim 1 wherein the step of anchoring the stem and the implant anchor from a proximal end of the bone tunnel further comprises:
    inserting a fixation element into the bone tunnel;
    ensuring the stem is secured to the implant anchor; and
    engaging the stem with the fixation element whereby the fixation element anchors the implant anchor on the first joint surface.

3. The method of claim 1 wherein the first implant system comprises a humeral head implant system.

4. The method of claim 1 wherein:
    the first implant system further comprises a fixation element;
    the fixation element having a fixation element end and an anchor end;
    the anchor end of the fixation element configured to couple with the implant anchor; and
    the fixation element end configured to be secured to the bone whereby when the fixation element is secured to the bone, the fixation element secures the implant anchor to the bone.

5. The method of claim 1 wherein:
    the first implant system is a humeral head implant system and the bone is a humeral head; and
    the second implant anchor is an element in a glenoid implant system and the second joint surface is a glenoid joint surface.

6. The method of claim 1 wherein:
    the first implant system is configured to be used as a humeral head implant secured to a humerus;
    a joint surface of the implant surface cap comprises an articulating surface of the humeral head implant; and
    the second implant anchor is an element in a glenoid implant having a glenoid surface whereby when the glenoid implant is secured into a second bone the glenoid surface creates an articulating surface for the glenoid implant to engage the articulating surface of the humeral head implant.

7. The method of claim 1 wherein the second implant anchor is an element of a second implant system wherein the second implant system comprises:
    the second implant anchor having an implant anchor retaining element;
    a second implant surface cap with a second cap retaining element;
    the second cap retaining element is configured to couple with the implant anchor retaining element whereby the second implant surface cap is coupled to the second implant anchor; and
    the second implant system is configured to be used as a glenoid implant.

8. The method of claim 1 wherein the second implant anchor is an element of a glenoid implant system.

9. The method of claim 1 wherein the first reaming blade further comprises a concave reaming surface.

10. The method of claim 9 wherein the first reaming blade further comprises a reaming blade shape of one selected from the group consisting of:
    an x-shape;
    a circular shape; and
    a ring shape with a cross member.

11. The method of claim 1 wherein the second reaming blade further comprises a convex reaming surface.

12. The method of claim 11 wherein the second reaming blade further comprises a reaming blade shape of one selected from the group consisting of:
- an elongated shape;
- a cross shape;
- a circular shape; and
- a ring shape with a cross bar.

13. The method of claim 1 wherein the implant anchor comprises one selected from the group consisting of:
- an implant anchor configured to be secured on the first joint surface utilizing the stem and a fixation element; and
- an implant anchor configured to be secured on the first joint surface utilizing an anchor retaining element.

14. The method of claim 1 wherein the second implant anchor comprises one selected from the group consisting of:
- a second implant anchor configured to be secured on the second joint surface utilizing multiple pegs;
- a second implant anchor configured to be secured on the second joint surface utilizing one or more screws;
- a second implant anchor configured to be secured on the second joint surface utilizing a threaded screw with a morse taper; and
- a second implant anchor configured to be secured on the second joint surface utilizing a retaining element.

15. The method of claim 1 wherein:
- the second implant anchor is a glenoid implant anchor configured to be secured on the second joint surface utilizing multiple pegs or one or more screws; and
- the glenoid implant anchor is configured to secure a surface cap to the glenoid implant anchor.

16. The method of claim 2 wherein the fixation element comprises one selected from the group consisting of:
- a bolt;
- a bolt and washer type element;
- a bolt configured to advance into a bore of the stem; and
- a bolt configured to advance against the stem without a bore.

17. The method of claim 4 wherein the fixation element comprises one selected from the group consisting of:
- a bolt;
- a bolt and washer type element;
- a bolt configured to advance into a bore of the stem; and
- a bolt configured to advance against the stem without a bore.

18. The method of claim 1 wherein the first implant system further comprises:
- the implant anchor further comprising an anchor retaining element;
- the implant surface cap further comprising a cap retaining element; and
- the cap retaining element is configured to couple with the anchor retaining element whereby the implant surface cap can be secured to the implant anchor.

19. The method of claim 1 wherein the first implant system further comprises:
- a fixation element;
- the stem having a fixation element end and an anchor end;
- the anchor end of the stem configured to couple with the implant anchor; and
- the fixation element having a stem end configured to couple with the fixation element end of the stem whereby when the fixation element is secured to the bone, the fixation element secures the stem and the implant anchor to the bone.

20. The method of claim 1 wherein the first implant system further comprises:
- a fixation element;
- the stem having a fixation element end and an anchor end;
- the anchor end of the stem configured to secure the stem to the implant anchor;
- the fixation element having a stem end having a tapered outer periphery configured to extend into the fixation element end of the stem;
- the fixation element end of the stem comprises an outer surface and an internal bore configured to receive a portion of the stem end of the fixation element; and
- the fixation element end is configured to expand when the portion of the stem end is received in the internal bore of the stem whereby the outer surface of the fixation element end engages a wall of the bone tunnel and anchors the stem in the bone tunnel.

\* \* \* \* \*